United States Patent
Holt et al.

(10) Patent No.: US 6,693,189 B2
(45) Date of Patent: Feb. 17, 2004

(54) MATERIALS AND METHOD FOR TREATING OR PREVENTING PATHOGENIC FUNGAL INFECTION

(75) Inventors: Dennis A. Holt, Stow, MA (US); Terence P. Keenan, Cambridge, MA (US); Timothy P. Clackson, Cambridge, MA (US); Leonard Rozamus, Bedford, MA (US); Wu Yang, Chestnut Hill, MA (US); Michael Z. Gilman, Newton, MA (US)

(73) Assignee: Ariad Gene Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/902,180

(22) Filed: Jul. 10, 2001

(65) Prior Publication Data

US 2002/0165250 A1 Nov. 7, 2002

Related U.S. Application Data

(62) Division of application No. 09/101,616, filed on Nov. 2, 1998, now Pat. No. 6,258,823.
(60) Provisional application No. 60/048,307, filed on May 30, 1997, and provisional application No. 60/021,624, filed on Jul. 12, 1996.

(30) Foreign Application Priority Data

Jul. 14, 1997 (WO) .............................. PCT/US97/012584

(51) Int. Cl.$^7$ ...................... C07D 487/00; A61K 31/33; A61K 31/44
(52) U.S. Cl. ...................... 540/456; 514/183; 514/291
(58) Field of Search .......................... 540/456; 514/291, 514/183

(56) References Cited

U.S. PATENT DOCUMENTS

| | | | |
|---|---|---|---|
| 5,091,389 A | * 2/1992 | Ondeyka et al. | 514/291 |
| 5,100,883 A | 3/1992 | Schiehser | 514/183 |
| 5,151,413 A | * 9/1992 | Caufield et al. | 514/63 |
| 5,221,670 A | * 6/1993 | Caufield | 514/183 |
| 5,233,036 A | * 8/1993 | Hughes | 540/455 |
| 5,358,944 A | * 10/1994 | Caufield | 514/183 |
| 5,362,735 A | 11/1994 | Luengo | 514/291 |
| 5,378,696 A | * 1/1995 | Caufield | 514/183 |
| 5,491,229 A | 2/1996 | Shelley | 540/456 |
| 5,583,018 A | 12/1996 | Ford | 435/118 |
| 5,597,715 A | 1/1997 | Ford | 435/118 |
| 5,648,361 A | 7/1997 | Holt et al. | 514/291 |
| 5,661,156 A | 8/1997 | Holt et al. | 514/291 |
| 5,712,129 A | 1/1998 | Ford | 435/118 |
| 5,728,710 A | 3/1998 | Luengo | 514/291 |

FOREIGN PATENT DOCUMENTS

| | | |
|---|---|---|
| EP | 046 661 | 3/1982 |
| EP | 467 606 | 1/1992 |
| EP | 475 577 | 3/1992 |
| EP | 512 754 | 11/1992 |
| WO | WO 94/02136 | 2/1994 |
| WO | WO 94/02485 | 2/1994 |
| WO | WO 95/14023 | 5/1995 |
| WO | WO 98/16691 | 6/1995 |
| WO | WO 96/41807 | 12/1996 |

OTHER PUBLICATIONS

Luengo et al., (1995) Chemistry and Biology 2:471–481.
Shu et al., (1996) J. Labelled Compounds and Radiopharmaceuticals 38: 277–237.
Luengo et al., (1994) Tetrahedron Letters 35:6469–6472.
Luengo et al., (1994) J. Org. Chem 59:6512–6513.
Grinfeld et al., (1994) Tetrahedron Letter 35:6835–6838.
Chemical Abstracts vol. 119, No. 11, Sep. 13, 1993 Abstract #108571b.
Chemical Abstracts vol. 121, No. 21, Nov. 21, 1994 Abstract #255471p.
Goodman and Gilman, The Pharmacological Basis of Therapeutics Chapter 50, p. 1165–1175.

* cited by examiner

Primary Examiner—Kevin E. Weddington
(74) Attorney, Agent, or Firm—David L. Berstein

(57) ABSTRACT

This invention concerns derivatives of rapamycin and their antifungal uses. Also disclosed are materials and methods relevant to the identification of non-immunosuppressive anti-fungal rapamycin derivatives. Use of compounds, among others, of the formula

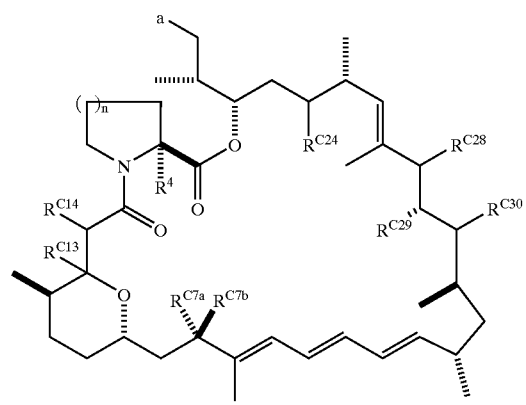

is disclosed, where the various substitutents are as defined.

9 Claims, No Drawings

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: FRAP-FRB consensus primer
<221> NAME/KEY: misc_feature
<222> LOCATION: (1)..(26)
<223> OTHER INFORMATION: FRAP-FRB consensus primer # 174
      where Y = C or T, R = A or G, N = A, C, G, or T

<400> SEQUENCE: 1
tggtayaarg cntggcayaa ytgggc                                    26

<210> SEQ ID NO 2
<211> LENGTH: 26
<212> TYPE: DNA
<213> ORGANISM: Artificial Sequence
<220> FEATURE:
<223> OTHER INFORMATION: FRAP-FRB consensus primer
<221> NAME/KEY: misc_feature
<222> LOCATION: (1)..(26)
<223> OTHER INFORMATION: FRAP-FRB consensus primer # 176
      where Y = C or T, R = A or G, N = A, G, C, or T.

<400> SEQUENCE: 2
gtnccnggna cngcyaaytc yaartc                                    26

<210> SEQ ID NO 3
<211> LENGTH: 8
<212> TYPE: PRT
<213> ORGANISM: Artificial Sequence
<220> FEATURE:
<223> OTHER INFORMATION: FRAP-FRB consensus region of primer #174
<221> NAME/KEY: SITE
<222> LOCATION: (1)..(8)
<223> OTHER INFORMATION: region coded for by the FRAP-FRB consensus primer #174

<400> SEQUENCE: 3

Trp Tyr Lys Ala Trp His Asn Trp
    1               5

<210> SEQ ID NO 4
<211> LENGTH: 9
<212> TYPE: PRT
<213> ORGANISM: Artificial Sequence
<220> FEATURE:
<223> OTHER INFORMATION: FRAP-FRB consensus region of primer #176
<221> NAME/KEY: SITE
<222> LOCATION: (1)..(9)
<223> OTHER INFORMATION: region coded for by FRAP-FRB consensus primer #176

<400> SEQUENCE: 4

Asp Leu Glu Leu Ala Val Pro Gly Thr
    1               5

<210> SEQ ID NO 5
<211> LENGTH: 420

```
<212> TYPE: DNA
<213> ORGANISM: C. neoformans
<220> FEATURE:
<221> NAME/KEY: misc_feature
<222> LOCATION: (1)..(420)
<223> OTHER INFORMATION: FRAP homolog

<400> SEQUENCE: 5
acccataaaa tgcgagagca ctctcccaag atcgttgacc aggccgagct tgtcagtact    60
    gagctcatcc gagcggctat cttatggcat gagatgtggt atgatggttt ggaagaagcg   120
    tcaaagcact actttggtga ccatgatatc cctggcatgc tgggagttct tgaacctttg   180
    catgagattg tcgaaaacgg accccaaacc ttgcgtgaga cgtcctttat tcaatcgttc   240
    gggcatgatt tgcgtatcgc ccgagagcat ctcaagcgtt accgtataac tcaggatggg   300
    accgaaattc aacaagcatg ggatgtctac tactccgtct tccagcgtct cggcaaacag   360
    ctcaagctcc tgaacgtcat tgagctgcaa tatgtctcgc ccaagttgat ggccgttcga   420

<210> SEQ ID NO 6
<211> LENGTH: 140
<212> TYPE: PRT
<213> ORGANISM: C.neoformans
<220> FEATURE:
<221> NAME/KEY: SITE
<222> LOCATION: (1)..(140)
<223> OTHER INFORMATION: FRAP homolog

<400> SEQUENCE: 6

Thr His Lys Met Arg Glu His Ser Pro Lys Ile Val Asp Gln Ala Glu
    1               5                   10                  15
    Leu Val Ser Thr Glu Leu Ile Arg Ala Ala Ile Leu Trp His Glu Met
                    20                  25                  30
    Trp Tyr Asp Gly Leu Glu Glu Ala Ser Lys His Tyr Phe Gly Asp His
                35                  40                  45
    Asp Ile Pro Gly Met Leu Gly Val Leu Glu Pro Leu His Glu Ile Val
            50                  55                  60
    Glu Asn Gly Pro Gln Thr Leu Arg Glu Thr Ser Phe Ile Gln Ser Phe
    65                  70                  75                  80
    Gly His Asp Leu Arg Ile Ala Arg Glu His Leu Lys Arg Tyr Arg Ile
                    85                  90                  95
    Thr Gln Asp Gly Thr Glu Ile Gln Gln Ala Trp Asp Val Tyr Tyr Ser
                    100                 105                 110
    Val Phe Gln Arg Leu Gly Lys Gln Leu Lys Leu Leu Asn Val Ile Glu
                115                 120                 125
    Leu Gln Tyr Val Ser Pro Lys Leu Met Ala Val Arg
                130                 135                 140
```

MATERIALS AND METHOD FOR TREATING OR PREVENTING PATHOGENIC FUNGAL INFECTION

RELATED APPLICATIONS

This application is a divisional application of U.S. Ser. No. 09/101,616 (filed Nov. 2, 1998) now U.S. Pat. No. 6,258,823, which claims the priority benefit of International Application PCT/US97/12584 (filed Jul. 14, 1997) which in turn claims the priority benefit as a continuation in part of U.S. Ser. No. 60/048,307 (filed May 30, 1997) and U.S. Ser. No. 60/021,624 (filed Jul. 12, 1996). The full contents of all the foregoing patent applications are hereby incorporated herein by reference.

BACKGROUND OF THE INVENTION

Rapamycin is a macrolide antibiotic produced by *Streptomyces hygroscopicus*. It was first identified by its antifungal activity but has been more often studied as an immunosuppressive agent.

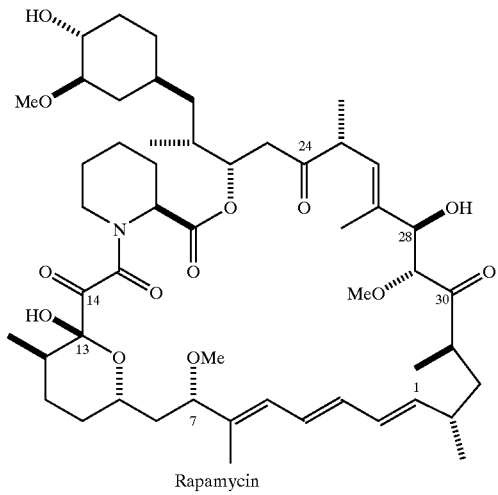

Rapamycin

A large number of structural variants of rapamycin have been reported, typically arising as alternative fermentation products or from synthetic efforts to improve the compound's therapeutic index as an immunosuppressive agent. For example, the extensive literature on analogs, homologs, derivatives and other compounds related structurally to rapamycin ("rapalogs") include among others variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. In nearly all cases, potent immunosuppressive activity is reported to accompany antifungal activity of the rapalogs. Additional historical information is presented in the background sections of U.S. Pat. Nos. 5,525,610; 5,310,903 and 5,362,718.

U.S. Pat. No. 5,527,907 is illustrative of the patent literature. That document discloses a series of compounds which were synthesized in an effort to make immunosuppressant rapalogs with reduced side effects. The compounds are disclosed via seven Markush structures, each followed by two to five or more columns of text listing possible substituents at various positions on the rapamycin ring. The document includes over 180 synthetic examples. The many variants of that invention were reported to be potent immunosuppressive agents.

While rapamycin is known to adversely affect the growth of fungi such as *Candida albicans* and *Microsporum gypseum*, its potent immunosuppressive activity renders it an unlikely candidate for use as an antifungal agent. Even some of the more recent patent documents such as WO 94102136 (SmithKline Beecham), WO 95116691 (Sandoz), U.S. Pat. No. 5,583,139 (Abbott) and U.S. Pat. No. 5,527,907 (Abbott), despite their extensive sets of structural modifications to rapamycin, fail to suggest even the possibility of reducing rapamycin's immunosuppressive activity without sacrificing its antifungal activity—let alone any structural approach for doing so—as would be desired or required in an antifungal agent. Indeed, the expectation that optimal response to any antifungal agent would require an active immune system in the treated patient appears to rule out the use of a rapalog. Thus it is not surprising that there are no known reports of the clinical development of rapamycin or a rapalog for treating or preventing infection by a pathogenic fungus in humans or other animals.

Meanwhile, although pathogenic fungi represent an increasing clinical challenge, existing antifungal agents are hampered by issues of efficacy, toxicity and the development and/or discovery of strains of pathogenic fungi that are resistant to drugs currently available or under development. By way of example, fungi that are pathogenic in humans include among others Candida spp. including *C. albicans, C. tropicalis, C. kefyr, C. krusei* and *C. galbrata*; Aspergillus spp. including *A. fumigatus* and *A. flavus*; *Cryptococcus neoformans*; Blastomyces spp. including *Blastomyces dermatitidis; Pneumocystis carinii; Coccidioides immitis; Basidiobolus ranarum*; Conidiobolus spp.; *Histoplasma capsulatum*; Rhizopus spp. including *R. oryzae* and *R. microsporus*; Cunninghamella spp.; Rhizomucor spp.; *Paracoccidioides brasiliensis; Pseudallescheria boydii; Rhinosporidium seeberi*; and *Sporothrix schenckii* [Kwon-Chung, K. J. and Bennett, J. E. (1992): Medical Mycology (Lea and Febiger, Malvern, Pa.)].

As described by Turner and Rodriguez, 1996, *Current Pharmaceutical Design*, 2, 209–224:

The need for new antifungal agents has never been greater. Over the past ten years the incidence of life-threatening fungal infections has increased dramatically as the population of immunocompromised individuals including cancer, organ transplant, and AIDS patients has increased.

Also contributing to this risk is the increased use of broad-spectrum antibiotics, increased use of invasive medical techniques, and an aging patient population.

While there is little in the literature to suggest the feasibility of any pharmaceutical approach for harnessing the antifungal activity of rapamycin or the rapalogs, non-immunosuppressive derivatives of rapamycin that retain anti-fungal activity would be of great interest for the treatment or prevention of pathogenic fungal infection.

SUMMARY OF THE INVENTION

In a distinct departure from the extensive literature of rapalog investigations, including results from some of the world's leading pharmaceutical research organizations, this invention provides, inter alia, a method and materials for treating or preventing infection by a pathogenic fungus in a mammalian subject, particularly a human patient, by administering to the subject a rapalog—but without causing untoward immunosuppression. The method comprises administering to the subject a composition comprising an effective antifungal amount of a non-immunosuppressive antifungal rapalog.

From a pharmaceutical perspective, this invention provides a method for preventing or treating a pathogenic fungus in a subject which involves administering to the subject a composition comprising a sub-immunosuppressive amount of a rapalog, e.g., administering the rapalog in an amount and manner which provides the intended antifungal effect but fails to impart an untoward immunosuppressive effect. Preferably the rapalog is a non-immunosuppressive antifungal rapalog.

Important applications of this invention include, among others, the treatment or prevention of infection in a patient by a pathogenic fungus such as those listed above or referred to below.

One aspect of this invention is the treatment or prevention of infection in a patient by a pathogenic fungus which is resistant to one or more other antifungal agents, especially an agent other than rapamycin or a rapalog, including e.g. amphotericin B or analogs or derivatives thereof (including 14(s)-hydroxyamphotericin B methyl ester, the hydrazide of amphotericin B with 1-amino-4-methylpiperazine, and other derivatives) or other polyene macrolide antibiotics, including, e.g., nystatin, candicidin, pimaricin and natamycin; flucytosine; griseofulvin; echinocandins or aureobasidins, incluing naturally occurring and semi-synthetic analogs; dihydrobenzo[a]napthacenequinones; nucleoside peptide antifungals including the polyoxins and nikkomycins; allylamines such as naftifine and other squalene epoxidease inhibitors; and azoles, imidazoles and triazoles such as, e.g., clotrimazole, miconazole, ketoconazole, econazole, butoconazole, oxiconazole, terconazole, itraconazole or fluconazole and the like. For additional conventional antifungal agents and new agents under deveopment, see e.g. Turner and Rodriguez, 1996, Recent Advances in the Medicinal Chemistry of Antifungal Agents, *Current Pharmaceutical Design*, 2, 209–224.

Another aspect of the invention is the treatment or prevention of infection in a patient by a pathogenic fungus in cases in which the patient is allergic to, otherwise intolerant of, or non-responsive to one or more other antifungal agents or in whom the use of other antifungal agents is otherwise contra-indicated. Those other antifungal agents include, among others, those antifungal agents disclosed above and elsewhere herein.

In the foregoing methods for treatment or prevention, a rapalog, preferably a non-immunosuppressive antifungal rapalog, is administered to the subject in an effective antifungal amount.

Another aspect of this invention is the treatment or prevention of infection by a pathogenic fungus in a patient by administration of a rapalog, preferably a non-immunosuppressive antifungal rapalog, in conjunction with the administration of one or more other antifungal agents, including for example, any of the previously mentioned agents or types of agents (e.g. in combination with treatment with amphotericin B, preferably in a lipid or liposome formulation; an azole or triazole such as fluconazole, for example; an aureobasidin; dihydrobenzo[a] napthacenequinone; or an echinocardin) as well as with a different rapalog. The rapalog may be administered before, after or at the same time the other antifungal agent is administered. In certain embodiments, the combination therapy will permit the use of reduced amounts of one or both antifungal components, relative to the amount used if used alone.

Another aspect of this invention is the treatment or prevention of infection by a pathogenic fungus in a patient by administration of a rapalog, preferably a non-immunosuppressive antifungal rapalog, in conjunction with the administration to the patient of one or more immune response modifiers, including for example, agents such as GM-CSF, M-CSF, IL-3, etc., preferably in an effective amount and regimen to alleviate neutropenia and/or other deficiency in immune function. The rapalog may be administered before, after or at the same time the immune response modifier is administered. Furthermore, the rapalog(s) and immune response modifier(s) may be administered in conjunction with the administration of one or more other antifungal agents, as mentioned previously.

Still another application of this invention involves administration of a rapalog to a subject for the treatment or prevention of infection by a pathogenic fungus, where the subject is immunosuppressed or immunocompromised, e.g. as the result of genetic disorder, disease such as diabetes or HIV or other infection, chemotherapy or radiation treatment for cancer or other disease, or drug- or otherwise induced immunosuppression in connection with tissue or organ transplantation or the treatment of an autoimmune disorder. Where the patient is being or will be treated with an immunosuppressive agent, e.g., in connection with a tissue or organ transplantation, a rapalog may be co-administered with the immunosuppressive agent(s) to treat or prevent a pathogenic fungal infection. Use of a non-immunosuppressive antifungal rapalog will be preferred to avoid unduly suppressing any residual immune function in the subject.

Another aspect of this invention is the treatment or prevention of infection by a pathogenic fungus in a patient infected, or suspected of being infected, with HIV, by administration of a rapalog, preferably a non-immunosuppressive antifungal rapalog, in conjunction with the administration of one or more anti-HIV therapeutics (including e.g. HIV protease inhibitors, reverse transcriptase inhibitors or anti-viral agents). The rapalog may be administered before, after or at the same time as administration of the anti-HIV agent(s).

Another aspect of this invention is the treatment or prevention of infection by a pathogenic fungus in a patient by administration of a rapalog, preferably a non-immunosuppressive antifungal rapalog, in conjunction with the administration of one or more other antibiotic compounds, especially one or more antibacterial agents, preferably in an effective amount and regiment to treat or prevent bacterial infection. Again, the rapalog may be administered before, after or at the same time as administration of the other agent(s).

Pathogenic fungal infections which may be treated or prevented by the methods of this invention include among others Aspergillosis, including invasive pulmonary aspergillosis; Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantation or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormycosis; Paracoccidioidomycosis; and Sporotrichosis. It should be noted that administration of a composition comprising an antifungal amount of one or more rapalogs will be particularly useful for treating or preventing a pathogenic fungal infection in a mammalian subject where the fungus is resistant to one or more other antifungal therapies, or where the use of one or more other antifungal therapies is contraindicated, e.g., as mentioned above.

Antifungal pharmaceutical compositions containing at least one antifungal rapalog, which is preferably a non-immunosuppressive antifungal rapalog, are also provided for use in practicing the methods of this invention. Those pharmaceutical compositions may be packaged together with an appropriate package insert containing, inter alia, directions and information relating to their antifungal use. Pharmaceutical compositions are also provided which contain one or more rapalogs together with a second antifungal agent.

In addition, new classes of rapalogs are also provided herein for various uses. New rapalogs which are immunosuppressive may be used as such in place of or in combination with rapamycin, cyclosporin A, FK506 and the like.

DETAILED DESCRIPTION

Rapalogs

"Rapalogs" as that term is used herein denotes a class of compounds comprising the various analogs, homologs and derivatives of rapamycin and other compounds related structurally to rapamycin. "Rapalogs" include compounds other than rapamycin (or those rapamycin derivatives modified in comparison to rapamycin only with respect to saturation of one or more of the carbon—carbon double bonds at the 1, 2, 3, 4 or 5, 6 positions) which comprise the substructure shown in Formula I, bearing any number of a variety of substituents, and optionally unsaturated at one or more carbon—carbon bonds unless specified to the contrary herein.

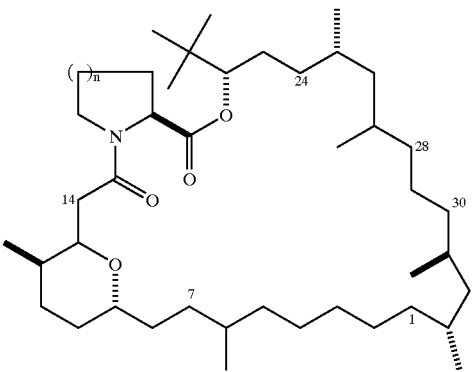

n = 1 or 2

Rapalogs include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and preferably do not contain an oxygen bridge between C1 and C30. Illustrative examples of rapalogs are disclosed in the documents listed in Table I. Examples of rapalogs modified at C7 are shown in Table II.

TABLE I

| | | | | |
|---|---|---|---|---|
| WO9710502 | WO9418207 | WO9304680 | US5527907 | US5225403 |
| WO9641807 | WO9410843 | WO9214737 | US5484799 | US5221625 |
| WO9635423 | WO9409010 | WO9205179 | US5457194 | US5210030 |
| WO9603430 | WO9404540 | US5604234 | US5457182 | US5208241 |
| WO9600282 | WO9402485 | US5597715 | US5362735 | US5200411 |
| WO9516691 | WO9402137 | US5583139 | US5324644 | US5198421 |
| WO9515328 | WO9402136 | US5563172 | US5318895 | US5147877 |
| WO9507468 | WO9325533 | US5561228 | US5310903 | US5140018 |
| WO9504738 | WO9318043 | US5561137 | US5310901 | US5116756 |
| WO9504060 | WO9313663 | US5541193 | US5258389 | US5109112 |
| WO9425022 | WO9311130 | US5541189 | US5252732 | US5093338 |
| WO9421644 | WO9310122 | US5534632 | US5247076 | US5091389 |

TABLE II
Illustrative C7 rapalog structures
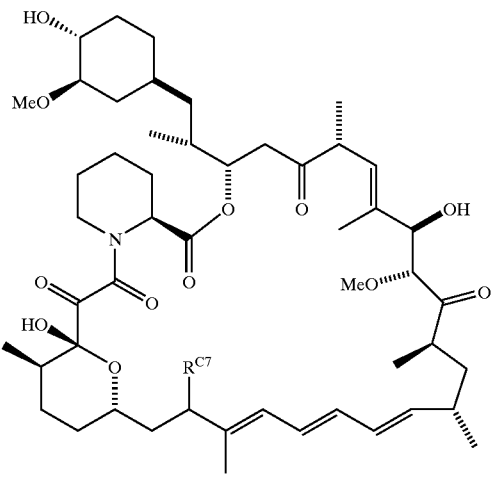
| $R^{C7}$ = | | | |
|---|---|---|---|
| ⁞⁞H | 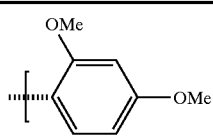 | ⁞⁞O—CH₂—Ar | Ar = phenyl, 3-nitrophenyl, 4-chlorophenyl, 3-iodo-4-diazophenyl, 3,4-dimethoxyphenyl, or 2-methoxyphenyl |
| ⁞⁞O-ipropyl | | | |
| —OMe | | | |
| ⁞⁞OH | | | |
| —OH | 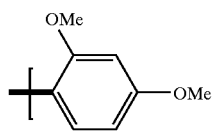 | —O—CH₂—Ar | Ar = 3,4-dimethoxyphenyl |
| ⁞⁞OEt | | | |
| —OEt | 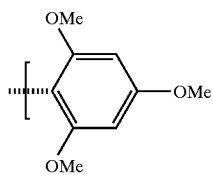 | —CH₂COPhenyl | |
| ⁞⁞OCH₂CH₂OH | | —OCHO | |
| —OCH₂CH₂OH | | | |
| ⁞⁞SMe | 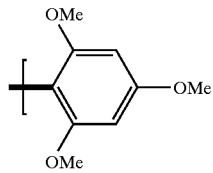 | —CH₂CH(OH)CH₂OH | |
| —SMe | | | |
| ⁞⁞SPhenyl | | —CH₂CH₂OCH₂CH₂OCH₂CH₂OCH₃ | |

TABLE II-continued
Illustrative C7 rapalog structures
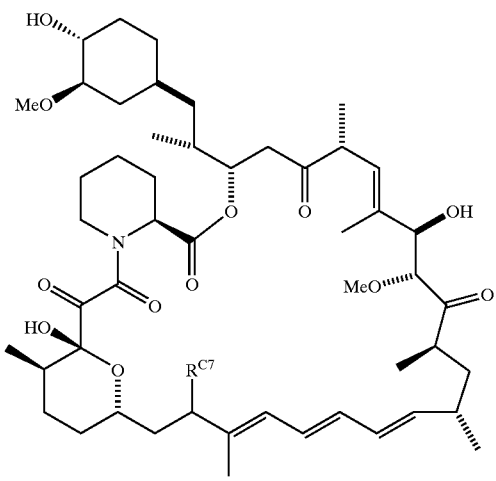
— SPhenyl
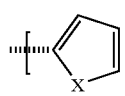
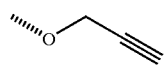
X = O or NH
⋯⋯ NHCO$_2$Me
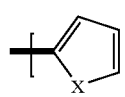
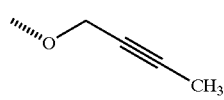
— NHCO$_2$Me
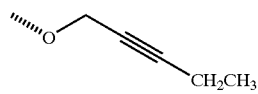
— Oacetyl
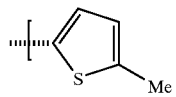
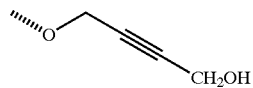
⋯⋯ O-nbutyl
⋯⋯ allyl
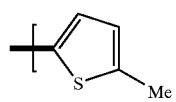
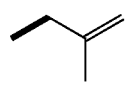
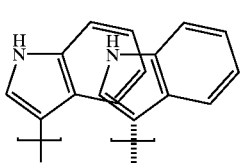

TABLE II-continued
Illustrative C7 rapalog structures
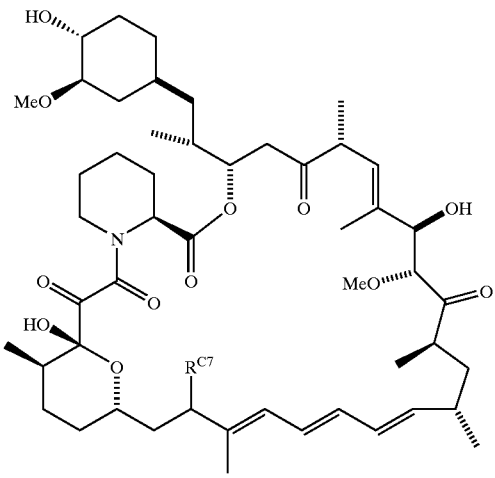
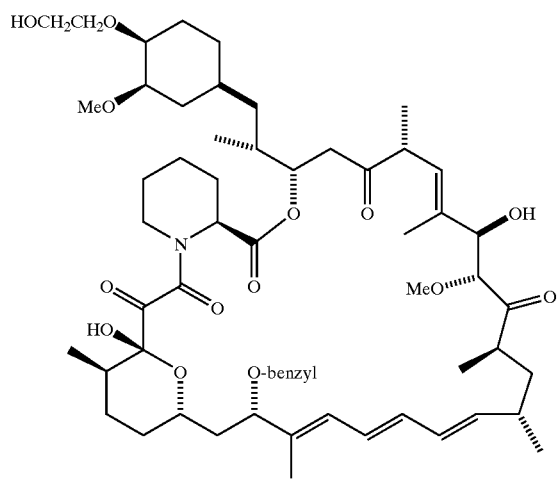
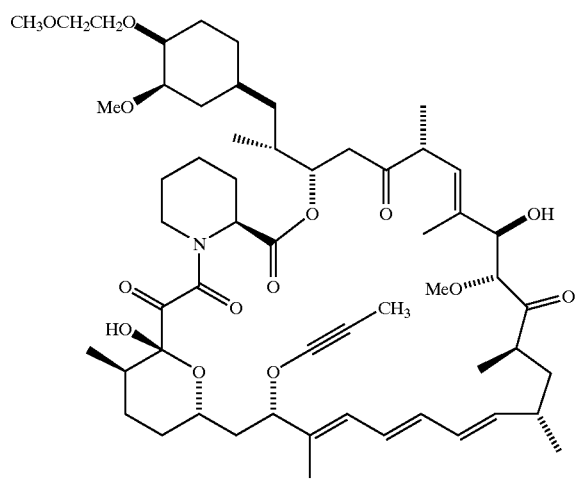

TABLE II-continued
Illustrative C7 rapalog structures
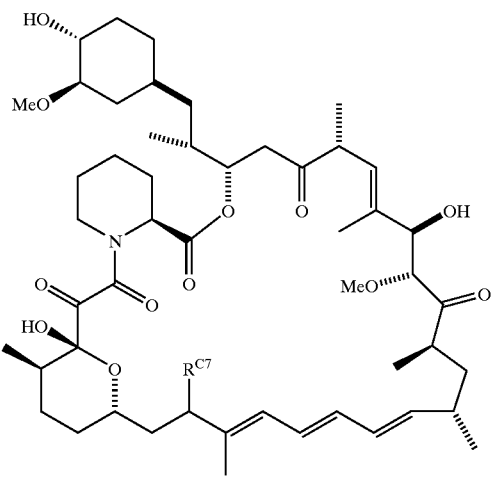
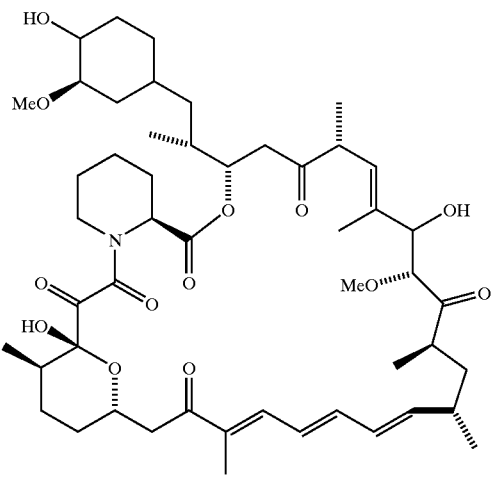
7-oxorapamycin
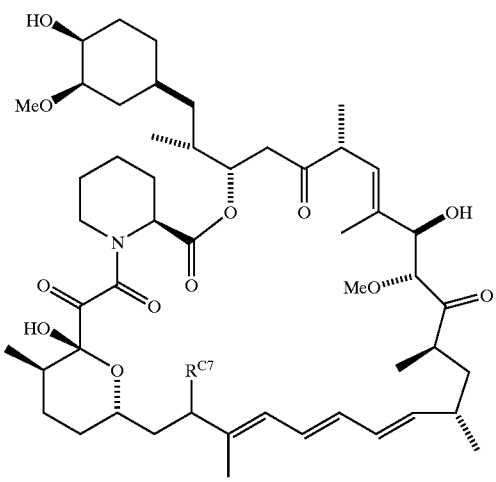
$$R^{C7} = \begin{bmatrix} \text{''''''H} \\ \text{''''''O-nbutyl} \\ \text{''''''allyl} \\ \text{—OMe} \end{bmatrix}$$
See e.g.,
Luengo et al, Chemistry & Biology, 1995, 2(7):471–481; JOC, 1995, 59(22):6512–13
WO 94/02136 (SmithKline Beecham)
WO 95/16691 (Sandoz)
US 5583139 (Abbott)

TABLE II-continued

Illustrative C7 rapalog structures

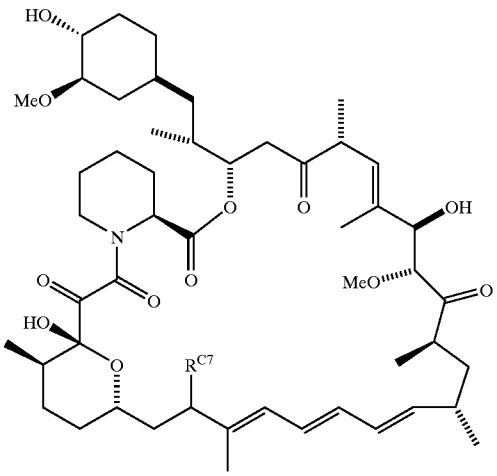

Grinfeld et al, 1994, Tett Letters 35(37):6835–6838
WO 96/41865 (ARIAD)

The relative antifungal activity of a given rapalog, in relation to rapamycin, may be quantified on a molar basis using any scientifically valid antifungal assay and a pathogenic fungal strain of interest. A variety of such antifungal assays, both in vitro and in vivo, are known in the art. By way of example, if the EC50 of a rapalog against a given pathogenic fungal strain is 6 nM and the EC50 of rapamycin against that strain is 2 nM, the relative antifungal activity ("AF") of the rapalog is 0.33. As is the case for all such comparisons, including the determination of relative immunosuppressive activity of a rapalog vs rapamycin discussed elsewhere herein, to be scientifically valid, the comparative data must be obtained through side-by-side comparison under identical conditions and must be repeated to achieve statistical significance.

Likewise, the relative immunosuppressive activity of a given rapalog, in relation to rapamycin, may be quantified on a molar basis using any scientifically valid test for immunosuppression in humans, or an appropriate surrogate therefor. Immunosuppression may be identified clinically as any detectable loss of immune function, e.g. decrease in T cell or B cell counts or decrease in T cell responsiveness to mitogenic stimulation. "Untoward immunosuppression", as that term is used herein, denotes the level or degree of immunosuppression which characteristically results from the administration of rapamycin to human patients in doses appropriate for immunosuppressive purposes. Untoward immunosuppression thus comprises a substantial decrease in one or more aspects of the patient's immune functions, or their sequellae, including circulating T and/or B cell levels, total white blood cell counts, responsiveness of T cells to mitogenic stimulation, delayed type hypersensitivity response, etc. One appropriate in vitro surrogate of immunosuppression in a human patient is inhibition of human T cell proliferation in vitro. This is a conventional assay approach that may be conducted in a number of well known variations using various human T cells or cells lines, including among others human PBLs and Jurkat cells. A rapalog may thus be assayed for human immunosuppressive activity and compared with rapamycin. A decrease in immunosuppressive activity relative to rapamycin measured in an appropriate in vitro assay is predictive of a decrease in immunosuppressive activity in humans, relative to rapamycin. Such in vitro assays may be used to evaluate the rapalog's relative immunosuppressive activity ("IS"). For example, if the EC50 of the rapalog in a human T cell proliferation assay is 400 nM, while that of rapamycin is 1 nM, then the IS value for the rapalog is 0.0025.

In the foregoing illustration, the rapalog had a relative antifungal activity-to-relative immunosuppressive activity ("AF/IS") ratio of 132 (i.e., 0.33/0.0025).

The term "non-immunosuppressive antifungal rapalog" is used herein to denote a rapalog that possesses an AF/IS value, with respect to at least one pathogenic fungal strain, of greater than 25, preferably greater than 100, more preferably greater than 500 and even more preferably greater than 1000. Especially preferred non-immunosuppressive antifungal rapalogs have an AF/IS ratio of 5000 or greater. Further discussion of non-immunosuppressive antifungal rapalogs with reference to chemical structure is provided below.

The term "sub-immunosuppressive amount" of a rapalog denotes a dose of a given rapalog that is insufficient to cause untoward immunosuppression.

Non-immunosuppressive, antifungal rapalogs include rapalogs that do not impart an untoward immunosuppressive effect when administered in an effective antifungal amount and dosing regimen. However, the rapalog need not be completely devoid of immunosuppressive effects, but should have less than 0.1, preferably less than 0.01, and even more preferably, less than 0.005 times the immunosuppressive effect observed or expected with an equimolar amount of rapamycin, as measured clinically or in an appropriate in vitro or in vivo surrogate of human immunosuppressive activity, preferably carried out on tissues of lymphoid origin.

Preferably, the selected non-immunosuppressive antifungal rapalog does not impart untoward other toxicity to the subject when administered in a manner and amount which allows it to provide its intended antifungal effect. Untoward other toxicity in this context is toxicity which prevents the use of the rapalog for antifungal therapy.

Rapalogs

This invention encompasses as new compositions of matter per se all non-immunosuppressive antifungal rapalogs other than those compounds depicted in Table II. One subset of such compounds of particular interest are those in which $R^{C7a}$ is other than —OMe, with reference to formula II. Based upon the findings of the present invention, the inventors believe that some of those rapalogs depicted in Table II, which were known at the time of the present invention, constitute non-immunosuppressive antifungal rapalogs. Those compounds depicted in Table II, as well as any other compounds previously reported, are not intended to be part of this invention as compounds per se. However, the pharmaceutical methods and related pharmaceutical materials, which are also very important parts of this invention, do in some embodiments encompass the use of any non-immunosuppressive antifungal rapalogs, including rapalogs depicted in Table II.

Rapalogs of particular interest for the practice of various aspects of this invention include compounds of formula II:

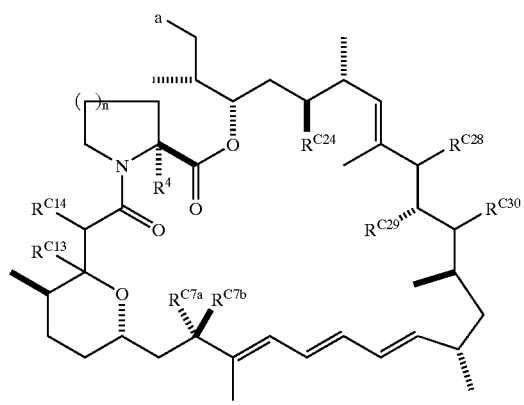

wherein

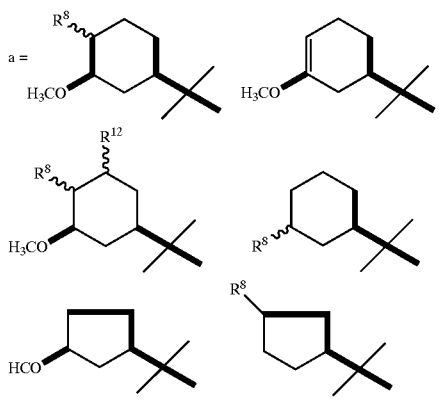

and, one of $R^{C7a}$ and $R^{C7b}$ is H and the other is —H, halo, —OR$^1$, —SR$^1$, —OC(O)R$^1$ or —OC(O)NHR$^1$, —NHR$^1$, —NR$^1$R$^2$, —NHC(O)R$^1$, —NH—SO$_2$—R$^1$ or —R$^2$, where R$^2$=aliphatic, heteroaliphatic, aryl, heteroaryl or alkylaryl (e.g. benzyl or substituted benzyl), $R^{C30}$ is halo, —OR$^3$ or (=O), $R^{C24}$ is =O, =NR$^4$=NOR$^4$ or =NNHR$^4$, —NHOR$^4$ or —NHNHR$^4$, —OR$^4$, —OC(O)R$^4$ or —OC(O)NR$^4$, halo or —H, $R^{C13}$ is H, halo, —OR$^5$, —OC(O)R$^5$, —OC(O)NHR$^5$, —SR$^5$, —SC(O)R$^5$, —SC(O)NHR$^5$, —NR$^5$R$^{5'}$, —N(R$^5$)(CO)R$^{5'}$ $R^{C14}$ is =O, —OR$^6$, —NR$^6$, —H, —NC(O)R$^6$, —OC(O)R$^6$ or —OC(O)NR$^6$ $R^3$ is H, —R$^7$, —C(O)R$^7$ or —C(O)NHR$^7$ or a cyclic moiety (e.g., carbonate) bridging C28 and C30

$R^{C28}$ is halo or —OR$^3$ $R^{C29}$ is H, OH or OMe where each ring substituent may be present in either stereochemical orientation unless otherwise indicated, and where R$^1$, R$^4$, R$^5$, R$^6$, R$^7$, R$^9$, R$^{10}$ and R$^{11}$ are independently selected from H, aliphatic, heteroaliphatic, aryl or heteroaryl;

and R$^8$ is H, halo, —CN, =O, —OH, —NR$^9$R$^{10}$, OSO$_2$CF$_3$, OSO$_2$F, OSO$_2$R$^{4'}$, OCOR$^{4'}$, OCONR$^{4'}$R$^{5'}$, or OCON(OR$^{4'}$)R$^{5'}$ (with the proviso that the compound is not rapamycin).

In rapamycin, $R^{C7a}$ is —OMe; $R^{C7b}$ is H; $R^{C14}$, $R^{C24}$ and $R^{C30}$ are each (=O); $R^{C13}$ and $R^{C28}$ are each —OH; $R^{C29}$ is OMe; and R$^3$ and R$^4$ are each H, all with the stereoisomerism as shown on page 1. Rapalogs of formula II useful in practicing this invention may contain substituents in any of the possible stereoisomeric orientations, and may comprise one stereoisomer substantially free of other stereoisomers (>90%, and preferably >95%, free from other stereoisomers on a molar basis) or may comprise a mixture of stereoisomers.

Also included are pharmaceutically acceptable derivatives of the foregoing compounds, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a rapalog as described herein, or a metabolite or residue thereof, preferably one which is an antifungal compound, and even more preferably, one which is a non-immunosuppressive antifungal agent. Pharmaceutically acceptable derivatives thus include among others pro-drugs of the rapalogs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Various pro-drugs of rapamycin and of other compounds, and materials and methods for derivatizing the parent compounds to create the pro-drugs, are known and may be adapted to the present invention.

The term "aliphatic" as used herein includes both saturated and unsaturated, straight chain (i.e., unbranched), branched, cyclic, or polycyclic aliphatic hydrocarbons, which are optionally substituted with one or more functional groups. Unless otherwise specified, alkyl, other aliphatic, alkoxy and acyl groups preferably contain 1–8, and in many cases 1–6, contiguous aliphatic carbon atoms. Illustrative aliphatic groups thus include, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Examples of substituents include: —OH, —OR$^{2'}$, —SH, —SR$^{2'}$, —CHO, =O, —COOH (or ester, carbamate, urea, oxime or carbonate thereof), —NH$_2$ (or substituted amine, amide, urea, carbamate or guanidino derivative thereof), halo, trihaloalkyl, cyano, —SO$_2$—CF$_3$, —OSO$_2$F, —OS(O)$_2$R$^{11}$, —SO$_2$—NHR$^{11}$, —NHSO$_2$—R$^{11}$, sulfate, sulfonate, aryl and heteroaryl moieties.

Aryl and heteroaryl substituents may themselves be substituted or unsubstituted (e.g. mono-, di- and trialkoxyphenyl; methylenedioxyphenyl or ethylenedioxyphenyl; halophenyl; or -phenyl-C(Me)$_2$—CH$_2$—O—CO—[C3–C6]alkyl or alkylamino).

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle" as used herein refers to cyclic heteroaliphatic groups and preferably three to ten ring atoms total, includes, but is not limited to, oxetane, tetrahydrofuranyl, tetrahydropyranyl, aziridine, azetidine, pyrrolidine, piperidine, morpholine, piperazine and the like.

The terms "aryl" and "heteroaryl" as used herein refer to stable mono- or polycyclic, heterocyclic, polycyclic, and polyheterocyclic unsaturated moieties having 3–14 carbon atom which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, e.g. phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —SO$_2$NH$_2$, —SO$_2$NH (aliphatic), —SO$_2$N(aliphatic)$_2$, —O-aliphatic-COOH, and —O-aliphatic-NH$_2$ (which may contain one or two N-aliphatic or N-acyl substituents).

A "halo" substituent according to the present invention may be a fluoro, chloro, bromo or iodo substituent. Fluoro is often the preferred halogen.

Compounds of formula II, exclusive of any compounds depicted in Table II, are of special interest and constitute an important class of novel compounds. Compounds of this class may differ from rapamycin with respect to one, two, three, four, five, six or seven substituent moieties. This class includes among others rapalogs with modifications, relative to rapamycin, at C7 and C13; C7 and C14; C7 and a; C7 and C43; C7 and C24; C7 and C28 C7 and C30; C7, C13 and C14; C7, C13 and a; C7, C13 and C43; C7, C13 and C24; C7, C13 and C28; C7, C13 and C30; C7, C14 and a; C7, C14 and C43; C7, C14 and C24; C7, C13 and C28; C7, C14 and C30; C7, a and C24; C7, a and C28; C7, a and C30; C7, C24 and C30; C7, C24, C30 and a; C7, C24, C30 and C13; C7, C24, C30 and C14; C24, C30 and C13; c24, C30 and a; C24, C30 and C14; and C24, C30, C13 and a, exclusive of any compounds depicted in Table II or otherwise previously reported publicly. Such compounds which comprise antifungal rapalogs, particularly those which constitute non-immunosuppressive antifungal rapalogs, are of special interest.

One subset of rapalogs of formula II of special interest for practicing the methods of this invention are those compounds (or pharmaceutically acceptable derivatives thereof) in which $R^{C7a}$ is a moiety other than OMe. This subset ("C7 rapalogs") includes compounds in which one of $R^{C7a}$ and $R^{C7b}$ is H and the other is selected from substituted or unsubstituted alkenyl, aryl, heteroaryl or —Z-aliphatic, Z-aryl, —Z-heteroaryl, or Z-acyl, where Z and Z' are independently O, S or NH and acyl comprises —CHO, —(C=O)-aliphatic, —(C=O)-aryl, —(C=O)-heteroaryl, —(C=O)—Z'-aliphatic, —(C=O)—Z'-aryl, —(C=O)—Z'-heteroaryl. In certain embodiments of this subset, $R^{C7a}$ and $R^{C7b}$ are independently selected from the following groups: H; a substituted or unsubstituted two to eight carbon straightchain, branched or cyclic alkenyl, alkoxyl or alkylmercapto; and a substituted or unsubstituted aryl, heteroaryl, aryloxy or heteroaryloxy, arylmercapto or heteroarylmercapto. Compounds of this subset include among others those in which $R^{C7a}$ is H; (together with $R^{C7b}$)=O; alkoxy; alkylmercapto; amino (1°, 2° or 3°); amido; carbamate; aryl or substituted aryl; phenyl or substituted phenyl; substituted or unsubstituted heteroaryl such as substituted or unsubstituted thiophenyl, furyl, indolyl, etc.; or benzyloxy or substituted benzyloxy. Other illustrative C7 rapalogs and types of C7 rapalogs which may be used in practicing the methods of this invention include those in which one of $R^{C7a}$ and $R^{C7b}$ is H and the other is selected from —OEt, —O-propyl, O-butyl, —OCH$_2$CH$_2$—OH, —O-benzyl, —O-substituted benzyl (including e.g., 3-nitro-, 4-chloro-, 3-iodo-4-diazo-, 3,4-dimethoxy-, and 2-methoxy-), —S—Me, —S-phenyl, —O(CO)Me, -allyl, —CH$_2$C(Me)=CH$_2$, —OCH$_2$—CCH, —OCH$_2$—CC—Me, —OCH$_2$—CC—Et, —OCH$_2$—CC—CH$_2$OH, or -2,4-dimethoxyphenyl, 2,4,6-trimethoxyphenyl, furanyl, thiophen-yl, methylthiophen-yl, pyrolyl and indolyl. In the foregoing types of rapalogs, the hydroxy substituent at C43 may be present in either stereochemical orientation or may be modified as described elsewhere herein. C7 rapalogs may further vary from rapamycin at one, two, three, four, five or more other positions as well. (Embodiments which do not differ from rapamycin at one or more other positions differ from rapamycin by deletion or replacement of the OMe moiety at C7a.) Non-immunosuppressive antifungal rapalogs of this subset are of particular interest. C7 rapalogs other than those depicted in Table II are novel and are encompassed by this invention as compositions of matter per se.

Another subset of rapalogs of formula II of interest in the practice of the various methods of the invention are C30, C24 rapalogs, i.e., rapalogs in which $R^{C30}$ and $R^{C24}$ are both other than (=O). Of special interest are those C30, C24 rapalogs in which $R^{C7a}$ is a moiety other than OMe. In certain embodiments of this subset, $R^{C7a}$ and $R^{C7b}$ are independently selected from —H, —OR$^1$, —SR$^1$, —OC(O)R$^1$ or —OC(O)NHR$^1$, —NHR$^1$, —NHC(O)R$^1$, —NH—SO$_2$—R$^1$ and —R$^2$, where R$^2$=substituted aryl or allyl or alkylaryl (e.g. benzyl or substituted benzyl), so long as one of $R^{C7a}$ and $R^{C7b}$ is H. In certain embodiments of this subset, $R^{C30}$ and $R^{C24}$ are both —OH, e.g. in the "S" configuration. In other embodiments $R^{C30}$ and $R^{C24}$ are independently selected from OR$^3$. This subset includes among others all rapalogs in which $R^{C30}$ and $R^{C24}$ are OH and the MeO substituent at C7 of rapamycin is replaced with any of the replacement substituents at that position identified in compounds of Table II. This subset includes among others rapalogs which differ from rapamycin only with respect to $R^{C30}$, $R^{C24}$ and either or both of $R^{C7a}$ and $R^{C7b}$. It also includes rapalogs which further differ from rapamycin with respect to the moiety a. For instance, this subset includes compounds of the formula:

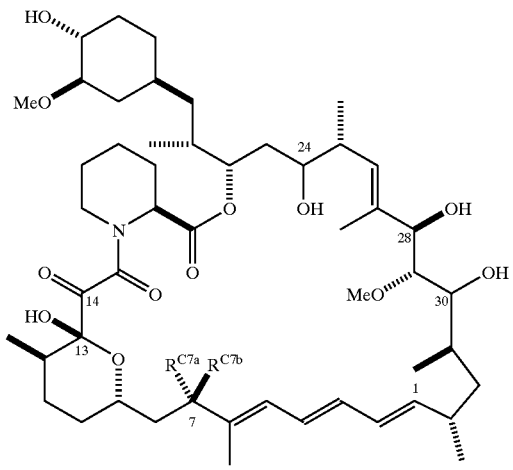

III where at least one of $R^{C7a}$ and $R^{C7b}$ is other than —OMe. Alternative substituents for $R^{C7a}$ and/or $R^{C7b}$ are as disclosed elsewhere herein. Of special interest are compounds in which one of $R^{C7a}$ and $R^{C7b}$ is cyclic aliphatic, aryl, heterocyclic or heteroaryl, which may be optionally substituted. Other compounds within this subset include those in which one, two, three, four or five of the hydroxyl groups is epimerized, fluorinated, alkylated, acylated or otherwise modified via other ester, carbamate, carbonate or urea formation. An illustrative compound for example is the compound of formula III in which the hydroxyl group at C43 is epimerized and the hydroxyl groups at C28 and C30 are alkylated, acylated or linked via carbonate formation.

Another subset of rapalogs of formula II of special interest are those compounds in which one or both of $R^{C13}$ and $R^{C28}$ is F. In various embodiments of this subset, one, two, three, four or five other substituents in formula II differ from the substituents found in rapamycin. For instance, this subset includes C13 fluororapalogs, C28 fluororapalogs and C13, C28-difluororapalogs of the following structures, where $R^{C7a}$ and $R^{C7b}$ are as previously defined:

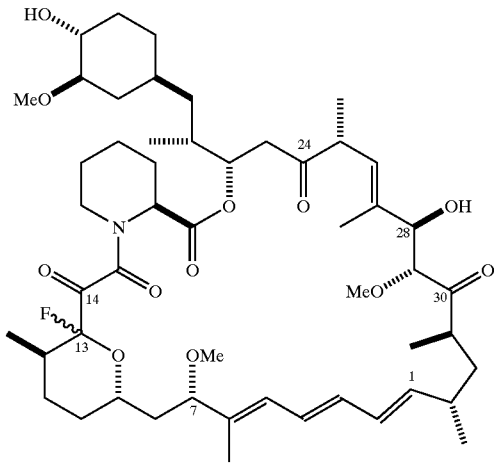

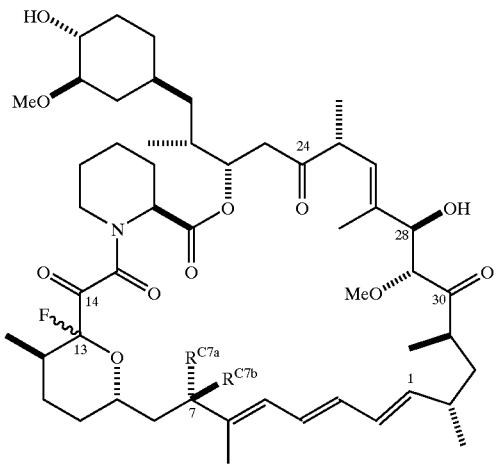
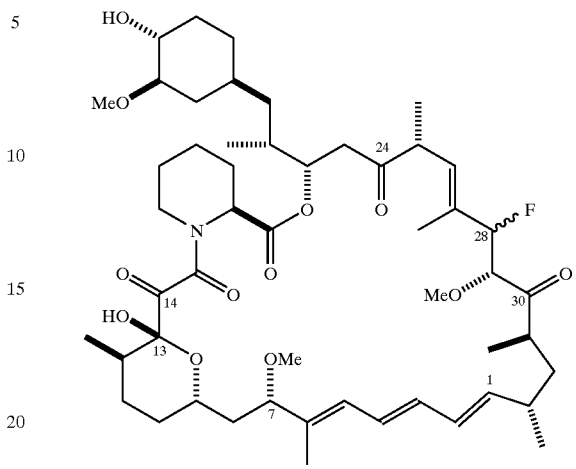
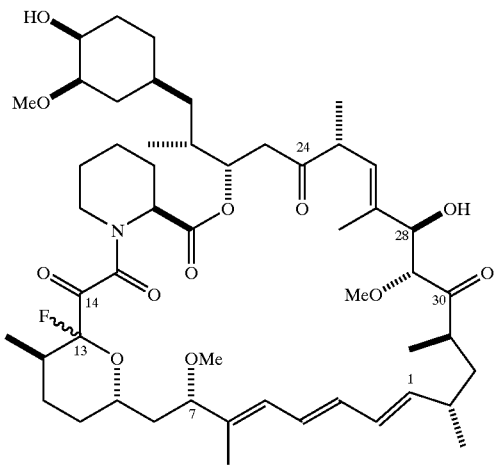
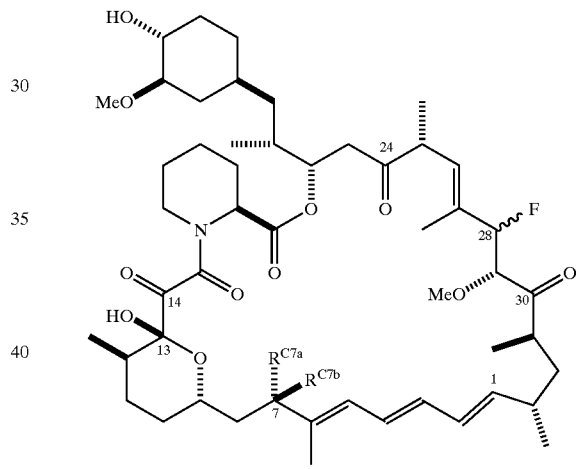
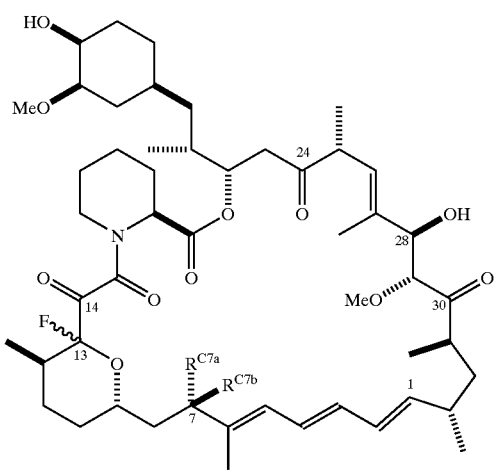
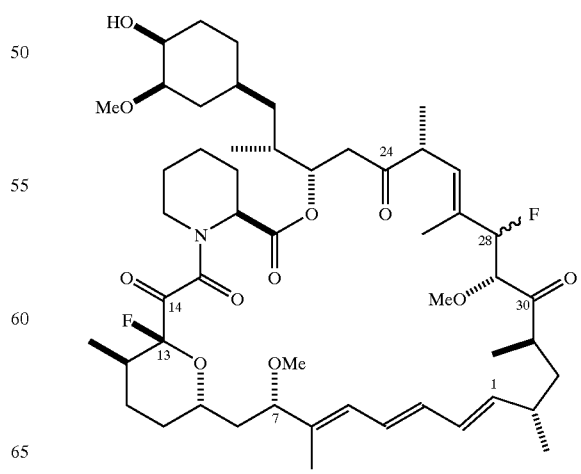

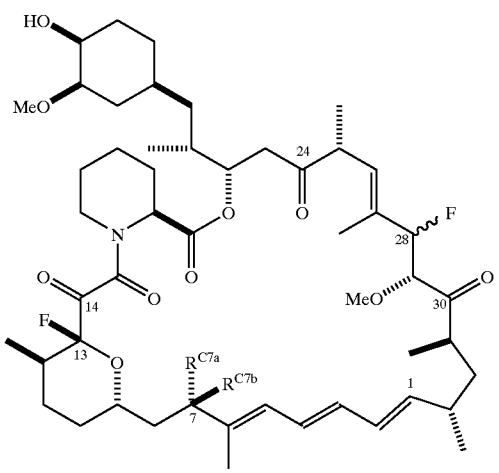

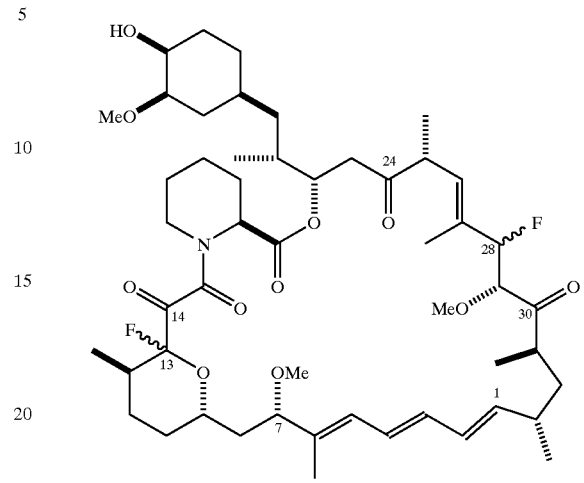

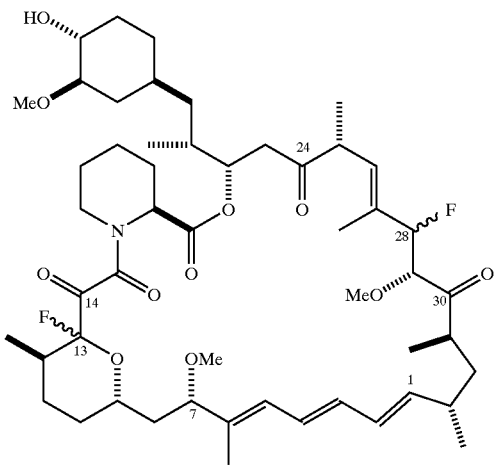

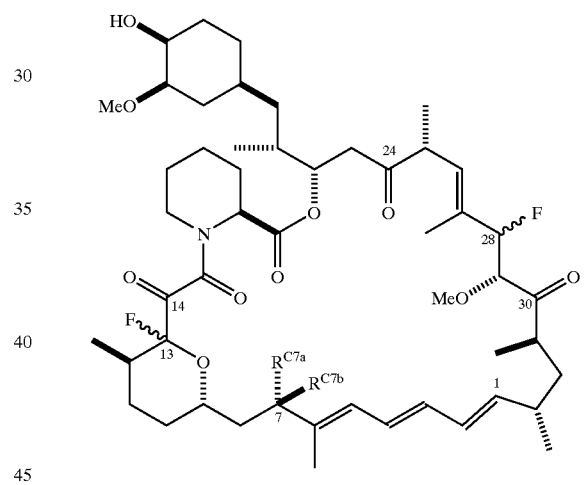

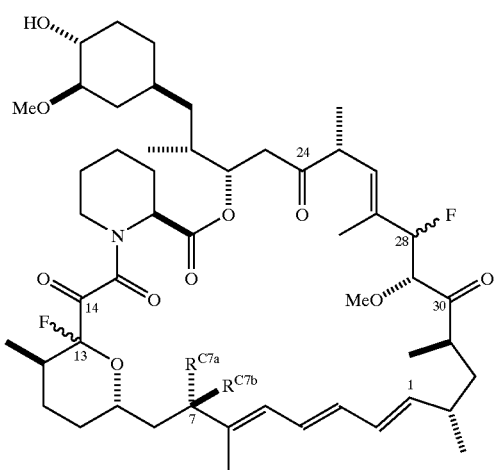

The 13-fluoro rapalogs, including in particular 13-fluoro rapamycin and analogs and derivatives thereof containing various substituents which are known to not abolish immunosuppressive activity in rapamycin itself, are of interest as immunosuppressants. Other variously substituted 13-fluoro rapalogs as well as other fluoro- and diflouro rapalogs, and in particular, those in which $R^{C7a}$ is other than OMe (e.g. aryl or heteroaryl or as otherwise exemplified herein) are of interest as antifungal agents.

An interesting intersection of some of the foregoing subsets of compounds is the set of rapalogs of formula II, or pharmaceutically acceptable derivatives thereof, in which $R^{C24}$ and $R^{C30}$ are both other than (=O) and one or both of $R^{C13}$ and $R^{C28}$ is F. This set includes, inter alia, 24,30-tetrahydro-13-F rapalogs, 24,30-tetrahydro-28-F rapalogs and 24,30-tetrahydro-13,28-diF rapalogs, as well as C7 variants of any of the foregoing, in which $R^{C7a}$ is other than OMe. A portion of that set is illustrated by the following structure, where $R^{C7a}$ and $R^{C7b}$ are as previously defined:

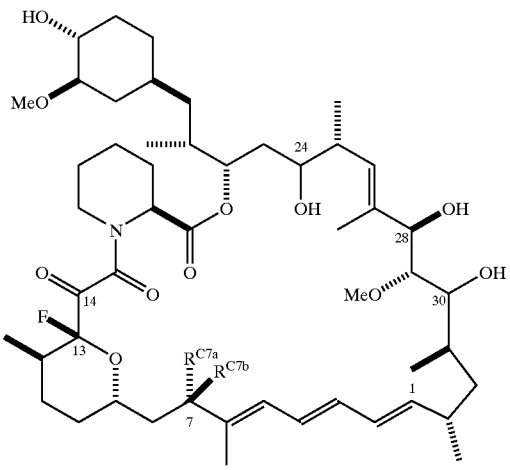

These compounds may be further derivatized, e.g., by modifications at one or both of $R^{C14}$ and $R^{C43}$ relative to the C14 and C43 substituents in rapamycin itself.

Another subset of compounds of formula II of special interest are those in which $R^{C14}$ is other than O, OH or H, e.g., compounds wherein $R^{C14}$ is —$OR^6$, —$NR^6$, —$NC(O)R^6$, —$OC(O)R^6$ or —$OC(O)NR^6$, with or without one or more other modifications relative to rapamycin.

Another subset of compounds of formula II of interest are those compounds in which $R^{C13}$ is other than an alkoxyl group comprising a C1–C4 alkyl moiety, with or without one or more other modifications at other positions relative to rapamycin. For example, this subset includes rapalogs which differ in structure from rapamycin by virtue of possessing (a) in place of OH at C13, a replacement substituent $R^{C13}$ which is other than C1–C4 alkoxy, and (b) in place of MeO at C7, replacement substituents $R^{C7a}$ and $R^{C7b}$ as defined above, Another subset of interest are compounds in which $R^{C24}$ is other than =O, again, with or without one or more other modifications at other positions relative to rapamycin.

Another subset of compounds of formula II which is of interest in practicing the methods of this invention include compounds which share the stereoisomerism of rapamycin and in which $R^{C7a}$ is —OMe wherein $R^{C30}$ is not =O, $R^{C24}$ is not =O, $R^{C13}$ is not —OH, $R^{C14}$ is not =O and/or $R^3$ and/or $R^4$ are not H.

Other compounds of interest include compounds of formula II in which $R^{C14}$ is OH.

Furthermore, this invention encompasses rapalogs in which one or more of the carbon—carbon double bonds at the 1, 2, 3, 4 or 5, 6 positions in rapamycin are saturated, if that modification is in combination with a modification elsewhere in the molecule, e.g. at one or more of C7, C13, C43, C24 C28 and/or C30. It should also be appreciated that the C3, C4 double bond may be epoxidized; that the C6 methyl group may be replaced with —$CH_2OH$ or —$CH_2OMe$; that the C43 hydroxy may be converted to F, Cl or H or other substituent; and that the C42 methoxy moiety may be demethylated, in any of the compounds disclosed herein, using methods known in the art. Likewise, moiety "a" may be replaced with any of the following

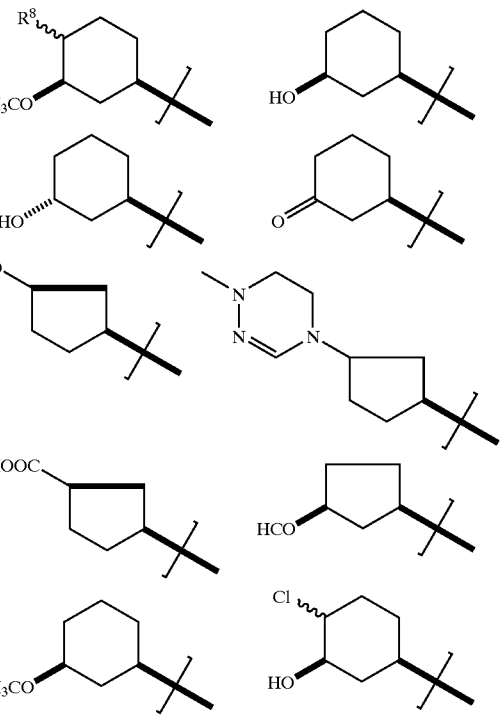

Non-immunosuppressive antifungal rapalogs of any of the foregoing subsets of compounds are considered of particular significance.

Compounds disclosed herein may be formulated with one or more pharmaceutically acceptable excipients, diluents, carriers, etc. to produce pharmaceutical or veterinary compositions for administration to human or other mammalian recipients, by any of various pharmaceutically approved routes, for the prevention or treatment of pathogenic fungal infection.

Rapalogs of the sort disclosed herein, including the various subsets and subclasses, may be administered to a patient in need thereof, as a method for treating or preventing infection by pathogenic fungi. In embodiments of this invention that involve administration of one or more non-immunosuppressive antifungal rapalogs, the administration of the rapalog(s) preferably does not lead to untoward immunosuppression in the recipient. The compound (s) is administered, typically in the form of a pharmaceutical or veterinary composition containing the compound(s) in admixture with one or more pharmaceutically acceptable carriers, diluents, buffers or other excipients, in an effective amount to prevent or inhibit fungal growth.

Synthetic Guidance

The production of rapamycin by fermentation and by total synthesis is known. The production of a number of rapalogs as fermentation products is also known. These include among others rapalogs bearing alternative moieties to the characteristic cyclohexyl ring or pipecolate ring of rapamycin, as well as C7-desmethyl-rapamycin, C29-desmethylrapamycin and C29-desmethoxyrapamycin.

Methods and materials for effecting various chemical transformations of rapamycin and structurally related macrolides are known in the art, as are methods for obtaining rapamycin and various rapalogs by fermentation. Many such chemical transformations of rapamycin and various rapalogs are disclosed in the patent documents identified in Table I, above, which serve to illustrate the level of skill and knowledge in the art of chemical synthesis and product recovery, purification and formulation which may be applied in practicing the subject invention. The following representative transformations and/or references which can be employed to produce the desired rapalogs are illustrative:

| ring position modified | literature reference |
| --- | --- |
| C7 | Luengo, el al. JOC 59, 6512 (1995); Chem & Biol 2(7), 471–481 (1995) |
| C-13 | C13→F: protect C28 and C43, rxn at 0° |
| C-14 | Schubert, et al. Angew Chem Int Ed Engl 23, 167 (1984). |
| C-20 | Nelson, U.S. Pat. No. 5,387,680 |

-continued

| ring position modified | literature reference |
| --- | --- |
| C-24 | U.S. Pat. No. 5,373,014; 5,378,836 Lane, et al. Synthesis 1975, p 136. |
| C-30 | Luengo et al. Tet. Lett. 35, 6469 (1994) |
| various positions | Or et al, U.S. Pat. Nos. 5,527,907 and 5,583,139 Luengo, WO 94/02136; Cottens et al, WO 95/16691 |

Approaches to the synthesis of the various fluoro and difluoro rapalogs are presented schematically below:

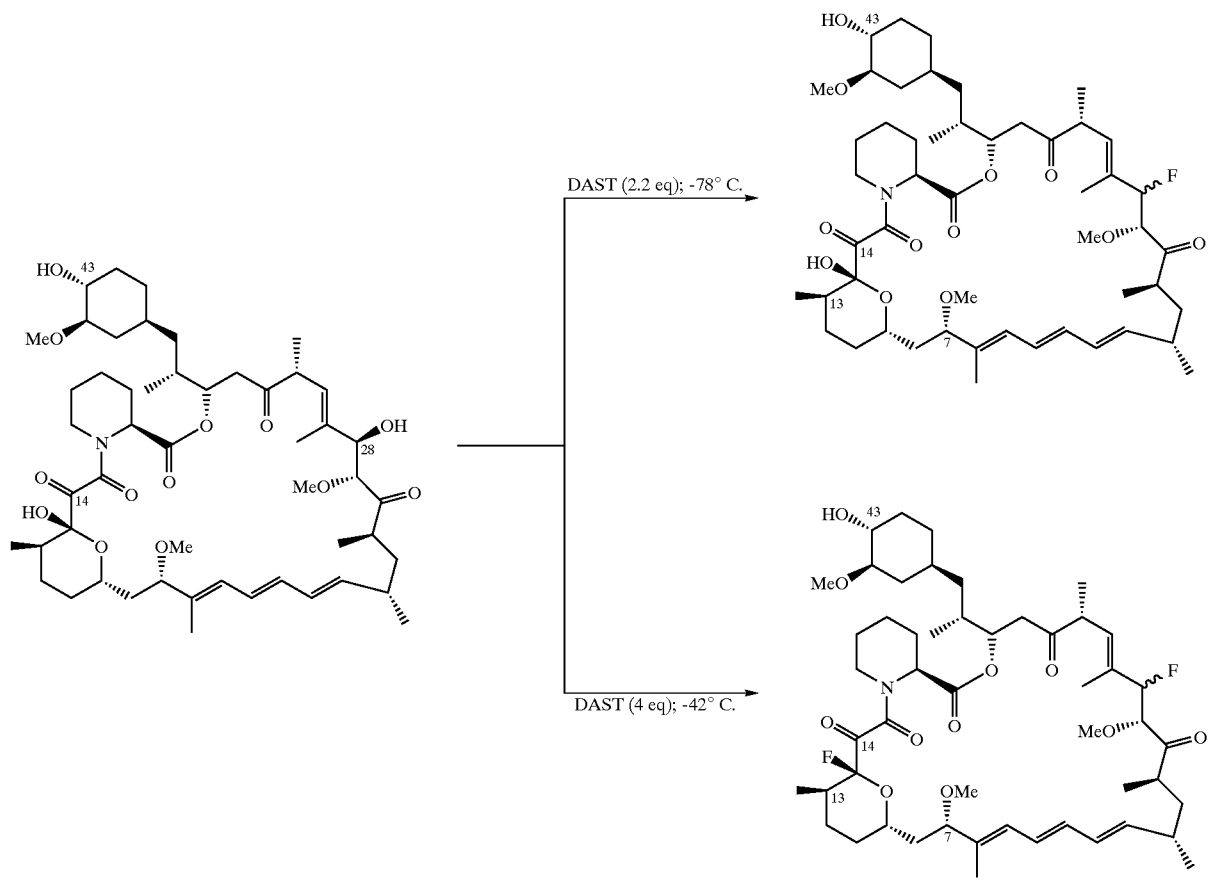

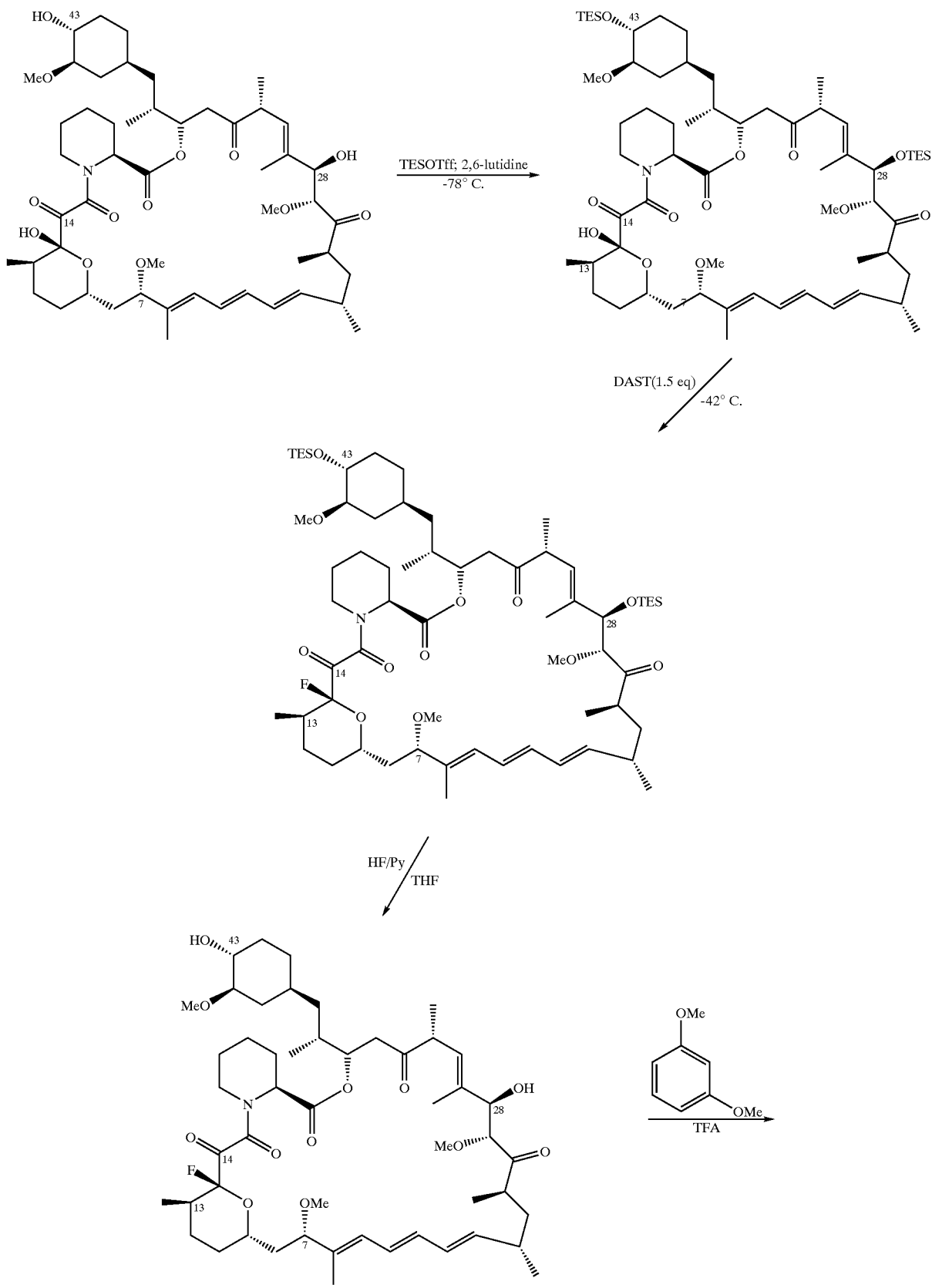
-continued

-continued
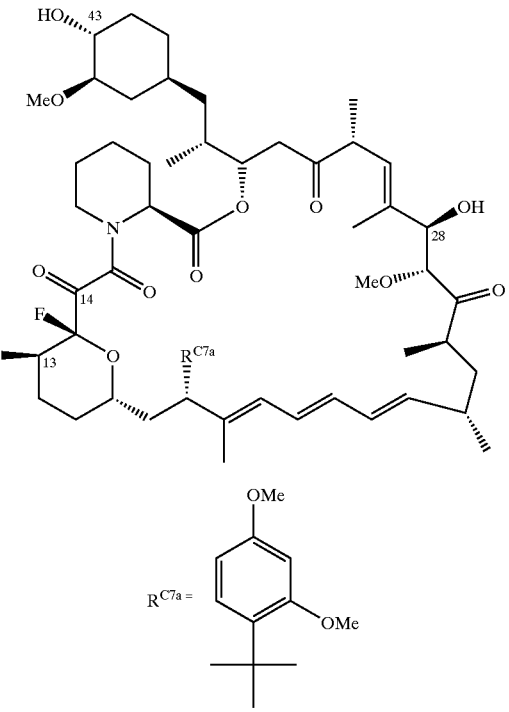
1. Smith, A. B. et al, J. Am. Chem. Soc. 1997, 119, 962–973.
2. Middleton, W. J, J. Org. Chem., 1975, 40, 574–578.
notes: The tri-isopropylsilyl homolog, TIPs, may be used in place of the triethylsilyl protecting moiety, TES.
 The DAST reaction on the doubly protected rapamycin may be co nducted at 0° C. if desired.
An approach to the synthesis of various 24,30-tetrahydrorapalogs is illustrated below:
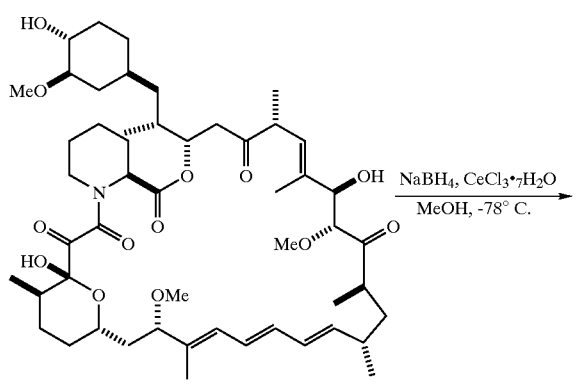
-continued
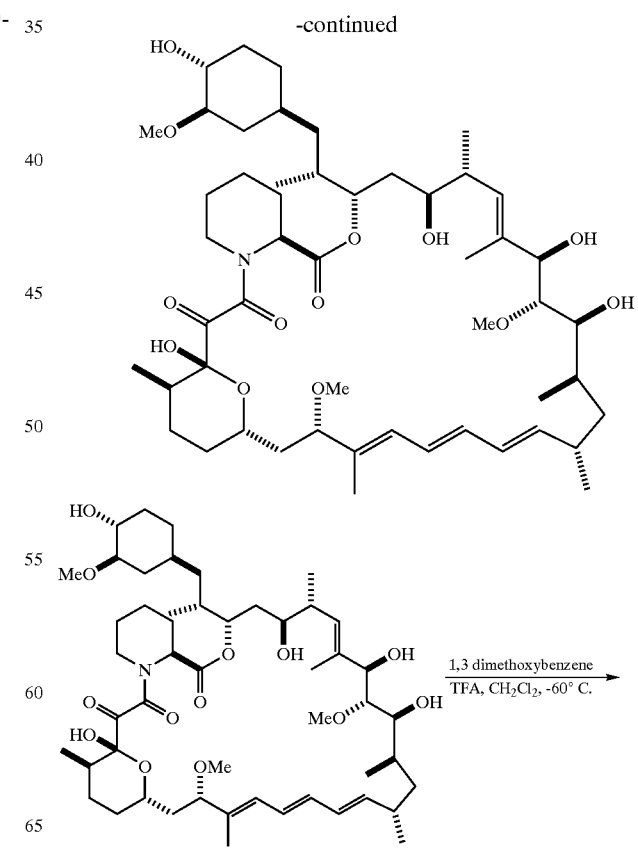

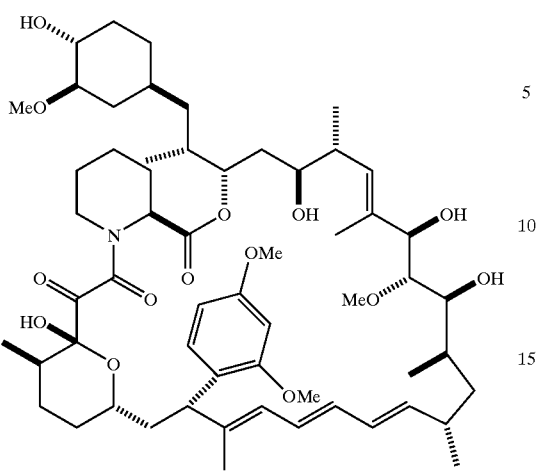
By way of further example, starting with 13-fluoro rapamycin instead of rapamycin yields the corresponding 13-fluoro-24,30-tetrahydro C7 rapalog.
One approach for the synthesis of other C13 derivatives is illustrated below:
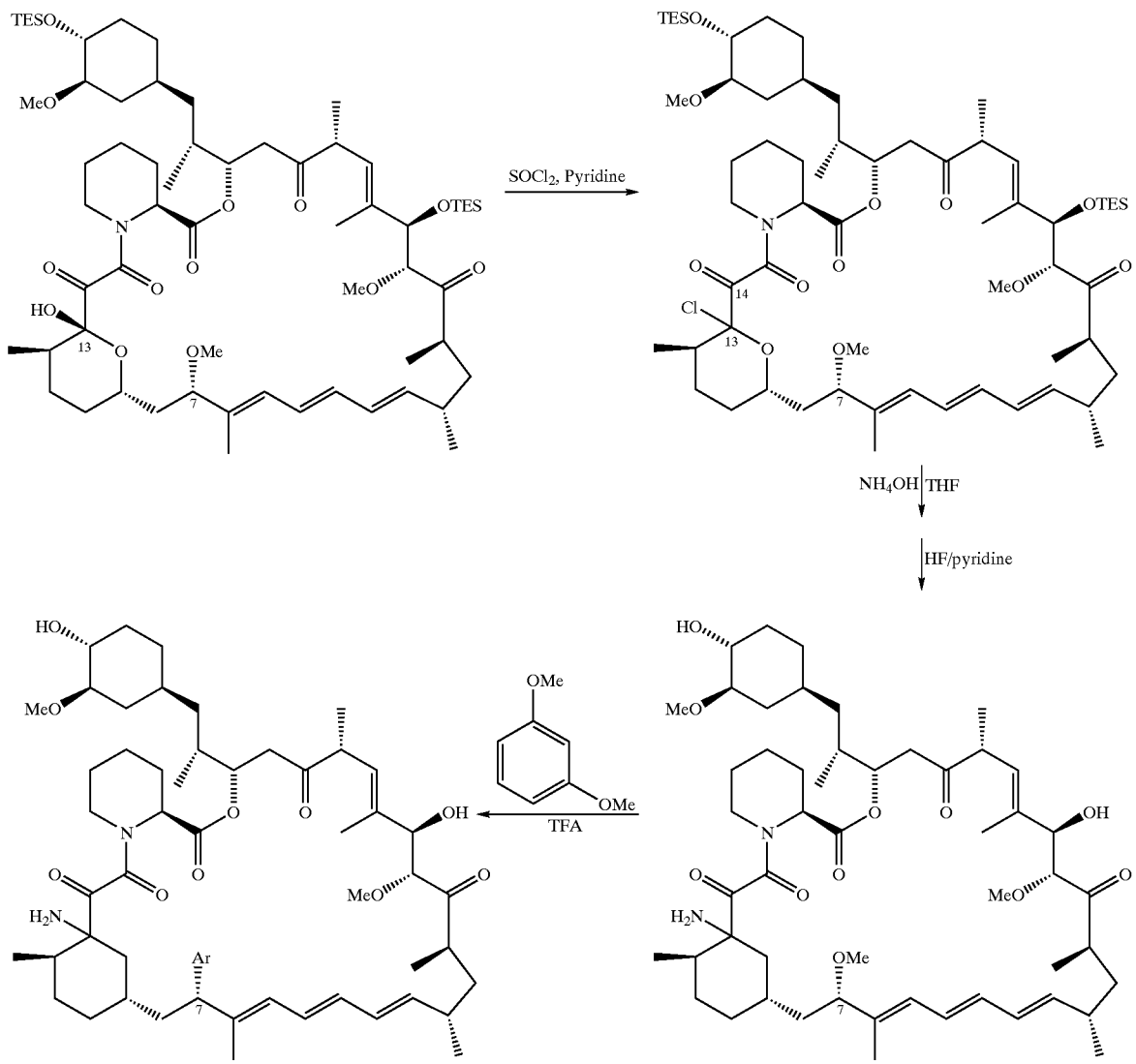
Donald, D. et al. WO91-13889

Additionally, it is contemplated that rapalogs for use in this invention as well as intermediates for the production of such rapalogs may be prepared by directed biosynthesis, e.g. as described by Katz et al, WO 93/13663 and by Cane et al, WO 9702358.

Non-immunosuppressive antifungal rapalogs and other novel rapalogs of this invention may be prepared by one of ordinary skill in this art relying upon methods and materials known in the art as guided by the disclosure presented herein. For instance, methods and materials may be adapted from known methods set forth or referenced in the documents cited above, the full contents of which are incorporated herein by reference. Additional guidance and examples are provided herein by way of illustration and further guidance to the practitioner. It should be understood that the chemist of ordinary skill in this art would be readily able to make modifications to the foregoing, e.g. to add appropriate protecting groups to sensitive moieties during synthesis, followed by removal of the protecting groups when no longer needed or desired, and would be readily capable of determining other synthetic approaches.

Assays for Human FKBP and FRAP Binding

Rapamycin is known to bind to the human protein, FKBP12, and to form a tripartite complex with hFKBP12 and FRAP, a human counterpart to the yeast proteins TOR1 and TOR2. Rapalogs may be characterized and compared to rapamycin with respect to their ability to bind to human FKBP12 and/or to form tripartite complexes with human FKBP12 and human FRAP (or fusion proteins or fragments containing its FRB domain). See WO 96/41865, the full contents of which are incorporated herein by reference. That application discloses various materials and methods which can be used to quantify the ability of a compound to bind to human FKBP12 or to form a tripartite complex with (i.e., "heterodimerize") proteins comprising human FKBP12 and the FRB domain of human FRAP, respectively. Such assays include fluorescence polarization assays to measure binding. Also included are cell based transcription assays in which the ability of a compound to form the tripartite complex is measured indirectly by correlation with the observed level of reporter gene product produced by engineered mammalian cells in the presence of the compound. Corresponding cell-based assays may also be conducted in engineered yeast cells. See e.g. WO 95/33052 (Berlin et al).

Human Immunzosuppression Assay Methods

Assays for immunosuppressive activity are known. By way of non-limiting example, immunosuppressive activity (as distinguished from binding activities) may be measured in a mitogenesis assay using human T cells. Such a human T cell proliferation assay is an example of an appropriate in vitro assay for use in determining an AF/IS value for a rapalog of interest.

In one embodiment, a representative compound can be evaluated in an in vivo test procedure designed to determine the survival time of pinch skin graft from male BALB/c donors transplanted to male C3H(H-2K) recipients. The method is adapted from Billingham et al. (1951) J. Exp. Biol. 28:385–402. Briefly, a pinch skin graft from the donor is grafted on the dorsum of the recipient as an allograft, and an isograft is used as control in the same region. The recipients are treated with either varying concentrations of a test rapalog compound intraperitoneally, intravenously or orally. Rapamycin can be used as a test control. Untreated recipients serve as rejection control. The graft is monitored daily and observations are recorded until the graft becomes dry and forms a blackened scab. This is considered as the rejection day. The mean graft survival time (number of days+/−S.D.) of the drug treatment group is compared with the control group. An ED50 value can be calculated as the mean ratio of weight rapalog to weight animal required to produce a mean graft survival time extending to the same period as control graft. The immunosuppressant activities, e.g., immunosuppressant ED50 values of the rapalog compounds of this invention can be determined via the hemolysin test in mice and by the delayed hypersensitivity test.

An exemplary hemolysin test is that described in Methods in Immunology, edited by D. H. Campbell et al, W. A. Benjamin, New York 1963 pages 172–175, and measures humoral or antibody response. The delayed hypersensitivity test measures the effect of a test rapalog compound on the ability of a subject mouse to mount a cell-mediated immune response to the antigen, Mycobacterium tuberculosis H37Ra. The mouse is sensitized to the antigen by subcutaneous administration in the base of the tail. The development of the delayed hypersensitivity response may be measured at any time beginning six days after sensitization but is usually done on the ninth day as follows: The right hind paw is injected with rapalog while the left hind paw (control) receives physiological saline. Both paw volumes are measured after twenty-four hours and significant increase in the volume of the right hind paw is taken as a measure of an effective delayed hypersensitivity response. All compounds are administered by the subcutaneous route. The expression ED50 (mg./kg.) is an expression of the number of milligrams of the rapalog per kilogram of body weight administered subcutaneously required to reduce the antibody activity by 50% when compared with a control. In this case, the lower the ED50 value for a rapalog the more potent an immunosuppressant it is.

The immunosuppressive activity of a rapalog may also be shown by a graft vs. host reaction (GVHR). In an illustrative embodiment, to induce a GVHR, C57 B1/6XA/J(F6AF1) male mice are injected intravenously with parental (C57B1/6J) spleen and lymph node cells. The compound (a rapalog) is then administered orally for 10 days beginning on the day prior to the cell transfer. On the day following the last treatment, the animals are sacrificed, and their spleens excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR. In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness (ED50) of the compounds administered to the mice in the experimental group is measured by comparing the spleen weight of the untreated and treated GVH animal with that of the syngeneic control. The ED50 value for immunosuppressive activity of rapalogs can also be measured according to the method of Takatsy et al. (1955) Acta. Microbiol. Acad. Sci. Hung., 3:105 or Cottney et at, (1980) Agents and Actions, 10:43.

The immunosuppressive activity of a rapalog may also be shown by a splenic atrophy test, e.g., a decrease in spleen weight after dosing BDF1 mice orally with the drug for seven (7) consecutive days. The mice are sacrificed on the eighth day. The percent decrease in spleen weight is measured for each dosage level.

Assays for Fungal FKBP and FRAP Binding

Compounds of formula II may be characterized and compared to rapamycin with respect to their ability to bind to the fungal counterpart of FKBP and/or to form a tripartite complex with that FKBP counterpart and a fungal FRAP or TOR counterpart, by analogy to the assay materials and methods referred to above ("Human Immunosuppression Assay Methods") using the fungal counterpart peptide sequences in place of human. A Candida FRAP counterpart sequence is provided in PCT/US95/06722 (Mitotix, Inc.). A Candida FKBP counterpart is also known. See Ferrara et al. (1992) Gene 113, 125–127 (Rapamycin Binding Protein, "RBP"). A Cryptococcus counterpart FRB sequence is provided below.

Assays for Activity Against Pathogenic Fungi

Comparative activity of a rapalog against a pathogenic fungus, relative to rapamycin, for use in determining the rapalog's AF/IS value is measured directly against the fungal organism, e.g. by microtiter plate adaptation of the NCCLS broth macrodilution method described in Diagn Micro and Infect Diseases 21:129–133 (1995). Antifungal activity can also be determined in whole-animal models of fungal infection. For instance, one may employ the steroid-treated mouse model of pulmonary mucormycosis [Goldani, L. Z. and Sugar, A. M. (1994) J. Antimicrob. Chemother. 33: 369–372]. By way of illustration, in such studies, a number of animals are given no rapalog, various doses of rapalog (and/or combinations with one or more other antifungal agents), or a positive control (e.g. Amphotericin B), respectively, beginning before, at the time of, or subsequent to infection with the fungus. Animals may be treated once every 24 hours with the selected dose of rapalog, positive control, or vehicle only. Treatment is continued for a predetermined number of days, e.g. up to ten days. Animals are observed for some time after the treatment period, e.g. for a total of three weeks, with mortality being assessed daily. Models can involve systemic, pulmonary, vaginal and other models of infection with or without other treatments (e.g. treatment with steroids) designed to mimic a human subject susceptible to infection.

To further illustrate, one method for determining the in vivo therapeutic efficacies (ED50, e.g., expressed in mg rapalog/kg subject), is a rodent model system. For example, a mouse is infected with the fungal pathogen such as by intravenous infection with approximately 10 times the 50% lethal dose of the pathogen ($10^6$ C. albicans cells/mouse). Immediately after the fungal infection, rapalog compounds are given to the mouse at a predetermined dosed volume. The ED50 is calculated by the method of Van der Waerden (Arch. Exp. Pathol. Pharmakol. 195 389–412, 1940) from the survival rate recorded on 20th day post-infection. Generally, untreated control animals die 7 to 13 days post-infection.

In another illustrative embodiment, C. albicans Wisconsin (C43) and C. tropicalis (C112), grown on Sabouraud dextrose agar (SDA) slants for 48 h at 28∫C., are suspended in saline and adjusted to 46% transmission at 550 nm on a spectrophotometer. The inoculum is further adjusted by hemacytometer and confirmed by plate counts to be approximately 1 or $5×10^7$ CFU/ml. CF-1 mice (white, male, ca. 20 g, Harlan Sprague Dawley, Inc., Indianapolis, Ind.) are infected by injection 1 or $5×10^6$ CFU into the tail vein. Antifungal agents are administered intravenously or subcutaneously in ethanol: water (10:90), 4 h post infection and once daily thereafter for 3 or 4 more days. Survival is monitored daily. The ED50 can be defined as that dose which allows for 50% survival of mice.

Cloning Fungal FKBP and FRB Domain Homologs to Facilitate Discovery and Development of Anti-Fungal Rapalogs The discovery and optimization of specific anti-fungal rapalogs may be aided by the cloning of FKBP and FRAP homologs or portions thereof from fungal pathogens. To that end, the publicly available nucleotide sequences encoding FRAPs from various species can be used to design degenerate PCR primers that will anneal to conserved regions that flank the FRB domain. This approach is illustrated in the cloning of the FRB counterpart from the pathogenic fungus *Cryptococcus neoformans*, below. cDNA or genomic DNA from target fungi can be amplified using these primers, and the products cloned and sequenced. Alternatively, known sequences can be used as probes (or can be used to design shorter synthetic oligonucleotide probes) that may be labeled and used to screen cDNA or genomic libraries prepared from pathogenic fungi, using standard methods. These procedures may analogously be used to isolate fungal FKBP homologs. The sequencers) of the FKBP homologs, and/or FRB domains from the FRAP homolog(s), can then be aligned with human and other known sequences to identify positions where amino acids differences occur.

Nucleotide sequences encoding FKBP and FRB homologs from fungal pathogens can be used in various ways to discover and improve anti-fungal rapalogs. For example, screens may be set up in which transcription of a reporter gene is dependent on the ability of rapamycin or a rapalog to heterodimerize two chimeric transcription factors, one containing at least one FKBP domain and one containing at least one FRB domain. Such assays can be conducted in mammalian cells using methods and materials as described in WO 96/41865, or in yeast cells using methods and materials as described in WO 95/33052, in either case substituting at least one, and preferably both fungal nucleotide sequences for the corresponding human nucleotide sequences. Since rapamycin's immunosuppressive activity in mammals, and the ability to inhibit cell growth in fungi, depend upon heterodimerization of endogenous FKBP and FRAP proteins, rapalog activity in the transcription assay is one approach for gauging the activity of the rapalog on cells from the organism from which the fused FKBP and FRB domains are derived. Thus, an assay using chimeric transcription factors containing fungal FKBP and/or FRB domains may be used to indirectly gauge the effects of various rapalogs on fungal growth. When only one of these fungal sequences is available, the other may be substituted by a known sequence from a related organism, for example FKB or TOR from *Candida albicans*, although this is not preferred. These assays may be useful for rank ordering of rapalogs for their propensity to interact with fungal FKBP and FRB proteins, e.g., as part of a rational program for optimizing antifungal activity. However, because this assay is not a direct measure of AF or IS activity, it is important that it not be used for determining AF or IS values for calculating AF/IS ratios.

Example 9, below, describes for the first time the cloning and nucleotide sequence of an FRB domain homolog from the pathogenic fungus *Cryptococcus neoformans*. This invention encompasses that nucleotide sequence; other nucleotide sequences encoding the same peptide sequence or a peptide sequence at least 90%, preferably at least 95%, identical thereto; nucleotides sequences encoding fragments thereof, preferably containing at least 15, more preferably at least about 25, and even more preferably, at least about 50 amino acid residues; nucleotide sequences encoding fusion proteins comprising part or all of the disclosed *C. neoformans* FRB peptide sequence together with peptide sequence derived from a different source; vectors containing any of the foregoing nucleotide sequences together with heterologous DNA comprising conventional genetic elements such as an origin of replication, promoter, enhancer, selectable marker, and the like, permitting cloning, transfection and heterologous expression in bacterial, yeast, insect or mammalian host cells; and cells into which such vectors have been introduced. Suitable vectors such as described above into which the nucleotide sequences may be ligated are well known in the art. Numerous types are commercially available and materials and methods for using them are well known and in widespread use. Nucleotide sequence encoding the *Cryptococcus neoformans* FRB may thus be used in a transcription assay as described in the previous paragraph in place of a nucleotide sequence encoding the FRB domain of human FRAP.

Another use for the nucleotide sequence of fungal FKBPs and FRB domains is in rational design of pathogen-specific rapalogs, that is, rapalogs that heterodimerize human FKBP and FRAP very poorly (leading to minimal immunosuppression), but which are able to heterodimerize the FKBP and FRAP proteins from fungus. This exploits the availability of the X-ray crystal structure of the ternary complex between human FKBP12, rapamycin, and the FRB domain of human FRAP. The predicted protein sequence of fungal FKBP and/or FRB domains may be used to construct a homology model of their three-dimensional structure using the coordinates of the human model as a starting point, using techniques and computer programs known in the art. These may be examined to identify regions near the interface between the protein(s) and rapamycin in the predicted ternary complex that are significantly different, and then to identify the position and design of substituents on the rapamycin molecule that would be accomodated selectively or specifically by the fungal proteins but not those of human and/or mammalian origin.

The use of sequence and modelling data to guide antifungal rapalog design may be illustrated by comparing the sequences of the FRB domains of human FRAP, *S. cerevisiae* TOR1 and TOR2, *Candida albicans* TOR FRB domain (WO 95/33052) and *Cryptococcus neoformans* TOR FRB domain (Example 9).

| species | residue at position 2098 (human numbering) |
|---|---|
| *H. sapiens* | Thr |
| *Saccharomyces cerevisiae* TOR 1 | Asn |
| *Saccharomyces cerevisiae* TOR 2 | Asn |
| *Candida albicans* | Asn |
| *Cryptococcus neoformans* | Gln |

Residue 2098 (human numbering) is threonine in the human sequence, asparagine in the *S. cerevisiae* and *C. albicans* sequences, and glutamine in *C. neoformans*. This residue is in direct contact with the C7-methoxy moiety of rapamycin in the crystal structure of the human ternary complex. Since only the human protein has a beta-branched amino acid sidechain at this position, there may be structural differences between the proteins that could be specifically or selectively recognized by C7 substituted rapalogs, when complexed with FKBP. This observation can serve as the basis of modeling as described above. A third use for the sequences of fungal FKBP and FRB homologs is the provision of direct structural information on rapalog binding, for iterative and rational drug design and optimization. The nucleotide sequences encoding the fungal polypeptides can be cloned into bacterial, insect and/or mammalian expression vectors and large amounts of protein expressed and purified, by methods well-known in the art. Nuclear magnetic resonance (nmr) and/or X-ray crystallographic procedures may be used to determine the three-dimensional structure of the proteins, either alone or in complex with rapalogs and/or partner proteins (FKBP for FRB, FRB for FKBP), from the same or different species. Solution of these structures can be facilitated markedly by using the technique of molecular replacement, using the coordinates of the human ternary complex as a starting model. Determination of the structure of fungal FKBP and FRB domains can be used to confirm the results of modelling (as described above), and identify further features unique to fungal proteins compared to those from mammals. Furthermore, the structures of the complexes between candidate anti-fungal rapalogs and fungal proteins can be used to confirm predictions of their mode of binding, and can be used to guide further modifications to enhance their affinity and/or selectivity.

Pharmaceutical Compositions

The present invention also pertains to pharmaceutical compositions containing at least one rapalog, preferably a non-immunosuppressive antifungal rapalog as described above and a pharmaceutically acceptable carrier forming a rapalog pharmaceutical composition. The rapalog will be present in an effective amount to prevent or treat pathogenic fungal infection when administered to a subject in need thereof. The pharmaceutical composition also can contain other additives which do not detrimentally affect the ability of the rapalog to perform its intended antifungal function, numerous examples of which are known in the art.

Rapamycin and the various rapalogs can exist in free form or, where appropriate or desired, in the form of a pharmaceutically acceptable derivative, including an ester, salt, etc. Pharmaceutically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids of bases. The compounds of the invention may form hydrates or solvates. It is known to those of skill in the art that charged compounds form hydrated species when lyophilized with water, or form solvated species when concentrated in a solution with an appropriate organic solvent.

The amount of the rapalog which will be effective in the treatment or prevention of a particular fungal pathogen will depend in part on the characteristics of the fungus and the extent of infection, and can be determined by standard clinical techniques. In vitro or in vivo assays may optionally be employed to help identify optimal dosage ranges. Effective doses may be extrapolated from dose-response curves derived from in vitro analysis or preferably from animal models. The precise dosage level should be determined by the attending physician or other health care provider and will depend upon well known factors, including route of administration, and the age, body weight, sex and general health of the individual; the nature, severity and clinical stage of the infection; the use (or not) of concomitant therapies.

The effective dose of the rapalog will typically be in the range of about 0.01 to about 50 mg/kgs, preferably about 0.1 to about 10 mg/kg of mammalian body weight per day, administered in single or multiple doses. Generally, the compound may be administered to patients in need of such treatment in a daily dose range of about 1 to about 2000 mg per patient. In embodiments in which the rapalog can result in some residual immunosuppressive effects, it is preferred that the dose administered be below that associated with untoward immunosuppressive effects.

The language "pharmaceutically acceptable carrier" is intended to include carriers or excipients which allow for administration of the rapalog to a subject in a manner in which it performs its intended antifungal function. Carriers include e.g. pharmaceutically acceptable grades of saline, buffered saline, dextrose, water, glycerol, ethanol, and combinations thereof, and are discussed in greater detail below. The composition, if desired, can also contain minor amounts of wetting or emulsifying agents, or pH buffering agents.

The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

Formulation may involve mixing, granulating and compressing or dissolving the ingredients as appropriate to the desired preparation. The pharmaceutical carrier employed may be, for example, either a solid or liquid. Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form. The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for rapamycin, and may be adapted to formulations for various rapalogs. A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension. To obtain a stable water soluble dosage form, a pharmaceutically acceptable salt of a rapalog may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the rapalog, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes.

The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary infection, preferred routes of administration are oral, nasal or via a bronchial aerosol or nebulizer. In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers. In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils. Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included. In addition, in certain instances, it is expected that the compound may be disposed within devices placed upon, in, or under the skin. Such devices include patches, implants, and injections which release the compound into the skin, by either passive or active release mechanisms. Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral administration). See also U.S. Pat. No. 5,362,735.

In a preferred embodiment, the rapalog is formulated for oral administration, as for example in the form of a solid tablet, pill, capsule, caplet or the like (collectively hereinafter "tablet") or an aqueous solution or suspension. In a preferred embodiment of the tablet form of the rapalog, the tablets are preferably formulated such that the amount of rapalog (or rapalogs) provided in 20 tablets, if taken together, would provide a dose of at least the median effective dose (ED50), e.g., the dose at which at least 50% of individuals exhibited the quantal effect of inhibition of fungal cell proliferation in vivo (or a statistically signficant reduction in infection). More preferably, the tablets are formulated such that the total amount of rapalog (or rapalogs) provided in 10, 5, 2 or 1 tablets would provide at least an ED50 dose to a patient (human or non-human mammal). In other embodiments, the amount of rapalog (or rapalogs) provided in 20, 10, 5 or 2 tablets taken in a 24 hour time period would provide a dosage regimen providing, on average, a mean plasma level of the rapalog(s) of at least the EC50 concentration (the concentration for 50% of maximal effect of, e.g., inhibiting fungal cell proliferation or statistically reducing the level fungal infection). An ED50 dose, for a human, is based on a body weight of from 10 lbs to 250 lbs, though more preferably for an adult in the range of 100 to 250 lbs. In preferred embodiments, a single dose of tablets (1–20 tablets) provides about 0.25 mg to 1250 mg of rapalog.

Likewise, the rapalogs can be formulated for parenteral administration, as for example, for subcutaneous, intramuscular or intravenous injection, e.g., the rapalog can be provided in a sterile solution or suspension (collectively hereinafter "injectable solution"). The injectable solution is preferably formulated such that the amount of rapalog (or rapalogs) provided in a 200 cc bolus injection would provide a dose of at least the median effective dose. More preferably, the injectable solution is formulated such that the total amount of rapalog (or rapalogs) provided in 100, 50, 25, 10, 5, 2.5, or 1 cc injections would provide an ED50 dose to a patient. In other embodiments, the amount of rapalog (or rapalogs) provided in a total volume of 100 cc to be injected at least twice in a 24 hour time period would provide a dosage regimen providing, on average, a mean plasma level of the rapalog(s) of at least the EC50 concentration. In preferred embodiments, a single dose injection provides about 0.25 mg to 1250 mg of rapalog. For continous intravenous infusion, e.g., drip or push, the rapalog can be provided in a sterile dilute solution or suspension (collectively hereinafter "i.v. injectable solution"). The i.v. injectable solution is preferably formulated such that the amount of rapalog (or rapalogs) provided in a 1 L solution would provide a dose, if administered over 15 minutes or less, of at least the median effective dose. More preferably, the i.v. injectable solution is formulated such that the total amount of rapalog (or rapalogs) provided in 1 L solution administered over 60, 90, 120 or 240 minutes would provide an ED50 dose to a patient. In preferred embodiments, a single i.v. "bag" provides about 0.25 mg to 5000 mg of rapalog per liter i.v. solution, more preferably 0.25 mg to 2500 mg, and even more preferably 0.25 mg to 1250 mg. As discussed above, the preferred rapalog pharmaceutical preparation, whether for injection or oral delivery (or other route of administration), would provide a dose less than the ED50 for immunosuppression in the host, more preferably at least 1 order of magnitude less, more preferably at least 2, 3 or 4 orders magnitude less. That is, the rapalog is dosed in sub-immunosuppressive amounts. In preferred embodiments, the amount of rapalog provided in the injectable or tablet will produce a maximal plasma concentration of the rapalog less than the EC50 for the rapalog.

Combination products which contain at least one rapalog as described above and an immunosuppressant agent such as FK506, rapamycin, cyclosporin A or the like; an antifungal agent such as amphotericin B, an analog or derivative thereof or another polyene macrolide antibiotic; flucytosine; griseofulvin; imidazole or triazole antifungal agent such as, e.g., clotrimazole, miconazole, ketoconazole, econazole, butoconazole, oxiconazole, terconazole, itraconazole or fluconazole, or another one or more antifungal agents such as are mentioned previously; one or more antibacterial agents; one or more antiviral agents or other agents for treating a patient infected with HIV such as are discussed above; or one or more immune response modifiers, may be formulated as described above or may be formulated based on formulation materials and methods used in connection with the other agent(s) in the combination. In the case of combination with one or more other antifungal agents, one or more active ingredients may be provided in reduced amounts (relative to amounts used in stand-alone products) by virtue of the combination. Alternatively, the rapalog and combination agent(s) may be separately formulated.

Packaged Rapalogs

The present invention also pertains to packaged rapalogs, preferably packaged non-immunosuppressive antifungal rapalogs, which term is intended to include at least one rapalog, as described above, packaged with instructions for administering the rapalog(s) as an antifungal agent without causing a untoward immunosuppressive effects within a human subject. In some embodiments, the non-immunosuppressive antifungal rapalog is a member of one of the preferred subsets of compounds described above. In certain embodiments, the non-immunosuppressive antifungal rapalog is a rapalog described in WO 94/02136, WO 95/16691, U.S. Pat. Nos. 5,583,139 or 5,527,907, the contents of each of which are incorporated herein by reference. The rapalog can be packaged alone with the instructions or can be packaged with another rapalog, rapamycin or another ingredient or additive, e.g., one or more of the ingredients of the pharmaceutical compositions of the invention. The package can contain one or more containers filled with one or more of the ingredients of the pharmaceutical compositions of the invention. Optionally associated with such container (s) can be a notice in the form prescribed by a governmental agency regulating the manufacture, use or sale of pharmaceutical or biological products, which notice reflects approval by the agency of manufacture, use or sale for human administration.

Methods of Treating Fungal Infections

The present invention further pertains to a method for treating or preventing a pathogenic fungal infection, including for example Aspergillosis, including invasive pulmonary aspergillosis; Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantaion or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormycosis; Paracoccidioidomycosis; and Sporotrichosis. The method involves administering at least one rapalog, preferably a non-immunosuppressive antifungal rapalog, as described above, to a human subject such that the fungal infection is treated or prevented without inducing an untoward immunosuppressive effect in the human subject. In some embodiments, the non-immunosuppressive antifungal rapalog is a member of one of the preferred subsets of compounds described above. In certain embodiments, the non-immunosuppressive antifungal rapalog is a rapalog described in WO 94/02136, WO 95116691, U.S. Pat. Nos. 5,583,139 or 5,527,907. In certain embodiments the rapalog is administered in conjunction with administration of one or more non-rapalog antifungal agents such as amphotericin B, or an imidazole or triazole agent such as those mentioned previously.

The pathogenic fungal infection may be topical, e.g., caused by, among other organisms, species of Candida, Trichophyton, Microsporum or Epidermophyton or mucosal, e.g., caused by *Candida albicans* (e.g. thrush and vaginal candidiasis). The infection may be systemic, e.g., caused by *Candida albicans, Cryptococcus neoformans, Aspergillus fumigatus*, Coccidiodes, Paracocciciodes, Histoplasma or Blastomyces spp. The infection may also involve eumycotic mycetoma, chromoblastomycosis, cryptococcal meningitits or phycomycosis.

In one embodiment, the method for treating or preventing a pathogenic fungal infection involves the administration of one or more rapalogs, preferably a non-immunosuppressive antifungal rapalog, to an immunocompromised subject. Preferably, the drug is administered to the immunocompromised subject without inducing an untoward further immunosuppressive effect. Examples of such subjects include subjects infected with HIV including patients with AIDS; immunosuppressed patients who have received, or are being treated with immunosuppressant therapy in preparation for receiving, an organ or tissue transplant, including e.g. bone marrow transplants; subjects having an autoimmune disorder or disease, e.g., diabetes, MS, myesthenia gravis, sytemic lupus erythmatosis or rheumatoid arthritis; and cancer patients who are immunosuppressed as a result of cancer chemotherapy or radiation therapy. It will often be preferred that the antifungal therapy spare any remaining immune function of the patient and that the rapalog be given in a sub-immunosuppressive dose or regimen. Where a rapalog is administered, it will be preferred in some such cases that the rapalog be a non-immunosuppressive antifungal rapalog. The rapalog may be administered in combination with one or more other antifungal agents to provide an antifungal therapy with a reduced dosage of one or more of the active ingredients as well as in the other combinations disclosed herein.

In another embodiment, the invention provides a method for treating or preventing a pathogenic fungal infection selected from the group consisting of Candida spp. including *C. albicans, C. tropicalis, C. kefyr, C. krusei* and *C. galbrata*; Aspergillus spp. including *A. fumigatus* and *A. flavus; Cryptococcus neoformans*; Blastomyces spp. including *Blastomyces dermatitidis; Pneumocystis carinii; Coccidioides immitis; Basidiobolus ranarum*; Conidiobolus spp.; *Histoplasma capsulatum*; Rhizopus spp. including *R. oryzae* and *R. microsporus*; Cunninghamella spp.; Rhizomucor spp.; *Paracoccidioides brasiliensis; Pseudallescheria boydii; Rhinosporidium seeberi*; and *Sporothrix schenckii*. Again, the method involves administering a non-immunosuppressive antifungal rapalog to a patient in need thereof such that the fungal infection is treated or prevented without inducing an untoward immunosuppressive effect.

In a further embodiment, the invention provides a method for treating or preventing a pathogenic fungal infection which is resistant to other antifungal therapy, including pathogenic fungal infections which are resistant to one or more antifungal agents mentioned elsewhere herein such as amphotericin B, flucytosine, one of the imidazoles or triazoles (including e.g. fluconazole, ketoconazole, itraconazole and the other previously mentioned examples). The method involves administering to the patient one or more rapalogs, preferably a non-immunosuppressive antifungal rapalog, in an amount and dosing regimen such that a fungal infection resistant to another antifungal therapy in the subject is treated or prevented.

In a further embodiment, the invention provides a method for treating or preventing a pathogenic fungal infection in a patient who is allergic to, intollerant of or not responsive to another antifungal therapy or in whom the use of other antifungal agents is otherwise contra-indicated, including one or more other antifungal agents mentioned elsewhere herein such as amphotericin B, flucytosine, one of the imidazoles or triazoles (including e.g. fluconazole, ketoconazole, itraconazole and the other previously mentioned examples). The method involves administering to such patient one or more rapalogs, preferably a non-immunosuppressive antifungal rapalog, in an amount such that a fungal infection is treated or prevented.

In each of the foregoing methods, the non-immunosuppressive antifungal rapalog may be a member of one of the preferred subsets of compounds described above, and in certain embodiments, the non-immunosuppressive antifungal rapalog is a rapalog described in WO 94/02136, WO 95/16691, U.S. Pat. Nos. 5,583,139 or 5,527,907.

A subset of the novel compounds disclosed herein, e.g. a subset of the 13-fluoro-rapalogs; 28-fluoro-rapalogs; 13,28- difluoro-rapalogs; 43-fluoro-rapalogs and 24,30-tetrahydro-rapalogs, retain immunosuppressive activity and are excluded from the class of non-immunosuppressive antifungal rapalogs as defined herein. These compounds may be used as immunosuppressive agents as alternatives to rapamycin itself. Thus, this invention further provides a method for inducing immunosuppression in a patient which comprises administering to the patient an immunosuppressive dose of one or more of the novel immunosuppressive rapalogs of this invention. Furthermore, this invention also provides a method for treating or preventing a pathogenic fungal infection in an immunocompromised patient which comprises administering to the immunocompromised patient a rapalog with antifungal activity, in an amount effective to treat or prevent infection by the pathogenic fungal organism. (It should be appreciated, however, that the subset of 13-fluoro-rapalogs; 28-fluoro-rapalogs; 13,28-difluoro-rapalogs; 43-fluoro-rapalogs and 24,30-tetrahydro-rapalogs which contain a C7a substituent other than OMe are of special interest for antifungal and dimerization uses.)

Other aspects of the invention include a method of producing a non-immunosuppressive, antifungal rapalog by modifying rapamycin to introduce (covalently) a moiety or substituent such that the resulting rapalog has the characteristics of an immunosuppressive, antifungal rapalog as defined previously. The invention also encompasses a method of formulating a non-immunosuppressive, antifungal rapalog pharmaceutical composition. This method involves combining a non-immunosuppressive, antifungal rapalog with a pharmaceutically acceptable carrier forming a non-immunosuppressive, antifungal rapalog pharmaceutical composition for the treatment or prevention of a pathogenic fungal infection without causing untoward immunosuppression.

The invention is further illustrated by the following examples which in no way should be construed as being further limiting. The contents of all references, pending patent applications and published patent applications, cited throughout this application are hereby incorporated by reference. It should be understood that the demonstration of efficacy in the assays of the examples is predictive of efficacy in humans.

EXAMPLES

1. Synthesis of Representative C-24 Modified Rapalogs

Example 1.1

Rapamycin Purification

Rapamycin was obtained by fermentation. The rapamycin producing organism, Streptomyces hygroscopicus (ATCC#29253), was cultivated on a complex media in 15 L or 30 L fed-batch fermentations. The biomass was harvested after 9–14 days by centrifugation. The supernatant was contacted for 1–2 hours with a nonionic, polymeric adsorbent resin, XAD-16 (Rohm and Haas). The adsorbent was recovered by centrifugation, combined with the biomass, and extracted repeatedly with methylene chloride. The solvent was removed in vacuo and the resulting residue extracted with acetonitrile which was then condensed in a similar manner. Chromatographic purification of the crude rapamycin was achieved by flash chromatography on silica gel (40% Acetone/Hexanes) followed by C-18 reversed-phase HPLC (70% $CH_3CN/H_2O$). Rapamycin obtained exhibited identical HPLC, spectroscopic, and biological characteristics as an authentic sample of rapamycin.

Example 1.2

Rapamycin (E and Z)-24-(O-methyloxime) (5, 6 (General Procedure)

A solution of rapamycin (60 mg 65.6 mmol) in MeOH (2 mL) was treated with NaOAc (22 mg 262 mmol, 4.0 eq) followed by methoxylamine hydrochloride (22 mg 262 mmol, 4.0 eq) and stirred at room temperature for 48 h. After this time the reaction mixture was quenched with $H_2O$ (10 mL) and extracted with EtOAc (3×10 ml). The combined organic extracts were washed with saturated NaCl solution (2×10 mL), dried over $Na_2SO_4$, filtered, and the solution concentrated in vacuo. The resulting residue was subjected to flash chromatography on silica gel (10% MeOH/dichloromethane) to afford a mixture of isomers. The isomer mixture was separated by HPLC (35%/E 25% $H_2O$/MeCN through a Kromasil C-18 250×20 mm column, 12 mL/min) to provide 13 mg (21%) of the faster eluting Z isomer and 7.6 mg (12%) of the E isomer. Z isomer: high-resolution mass spectrum (FAB) m/z 965.5749 [(M+Na)+, calcd for C, 52; H, 82; N, 2; $O_{13}Na$ 965.5710]. E isomer: high-resolution mass spectrum (FAB) m/z 965.5701 [(M+Na)+, calcd for C, 52; H, 82; N, 2; O, 13; Na, 965.5710;].

Example 1.3

Rapamycin (E and Z)-24-(O-ethyloxime) (7, 8)

Prepared in an analogous manner to Rapamycin (E and Z)-24-(O-methyloxime). The isomer mixture was separated by HPLC (30% $H_2O$/MeCN through a Kromasil C-18 250×20 mm column, 12 mL/min) to provide 7.7 mg (25%) of the faster eluting Z isomer and 0.5 mg (2%) of the E isomer. Z isomer: high-resolution mass spectrum (FAB) m/z 979.5902 [(M+Na)+, calcd for C, 53; H, 84; N, 2; O, 13; Na, 979.5871;].

Example 1.4

Rapamycin (E and Z)-24-(O-isobutyloxime) (9, 10)

Prepared in an analogous manner to Rapamycin (E and Z)-24-(O-methyloxime). The isomer mixture was separated by HPLC (15% $H_2O$/MeCN through a Kromasil C-18 250×20 mm column, 12 mL/min) to provide 28 mg (65%) of the faster eluting Z isomer and 3.0 mg (7%) of the E isomer. Z isomer: high-resolution mass spectrum (FAB) m/z 1007.6146 [(M+Na)+, calcd for C, 55; H, 88; N, 2; O, 13; Na, 1007.6184;]. E isomer: high-resolution mass spectrum (FAB) m/z 1007.6157 [(M+Na)+, calcd for C, 55; H, 88; N, 2; O, 13; Na, 1007.6184;].

Example 1.5

Rapamycin (E and Z)-24-(O-benzyloxime) (11, 12)

Prepared in an analogous manner to Rapamycin (E and Z)-24-(O-methyloxime). The isomer mixture was separated by HPLC (15% $H_2O$/MeCN through a Kromasil C-18 250×20 mm column, 12 mL/min) to provide 19.6 mg (44%) of the faster eluting Z isomer and 6.1 mg (14%) of the E isomer. Z isomer: high-resolution mass spectrum (FAB) m/z 1041.6033 [(M+Na)+, calcd for C, 58; H, 86; N, 2; O, 13; Na, 1041.6028;]. E isomer: high-resolution mass spectrum (FAB) m/z 1041.5988 [(M+Na)+, calcd for C, 58; H, 86; N, 2; O, 13; Na, 1041.6028;].

Example 1.6

Rapamycin (E and Z)-24-(O-carboxymethyloxime) (13, 14))

Prepared in an analogous manner to Rapamycin (E and Z)-24-(O-methyloxime). The isomer mixture was separated by HPLC (45% $H_2O$/MeCN through a Kromasil C-18 250×20 mm column, 12 mL/min) to provide 4.6 mg (11%) of the faster eluting Z isomer and 1.0 mg (2%) of the E isomer. Z isomer: high-resolution mass spectrum (FAB) m/z 1009.5664 [(M+Na)+, calcd for C, 53; H, 82; N, 2; O, 15; Na, 1009.5613;]. E isomer: high-resolution mass spectrum (FAB) m/z 1009.5604 [(M+Na)+, calcd for C, 53; H, 82; N, 2; O, 15; Na, 1009.5613];.

Example 1.7

Rapamycin (E and Z)-24-(O-carboxamidomethylexime) (15, 16)

Prepared in an analogous manner to Rapamycin (E and Z)-24-(O-methyloxime). The isomer mixture was separated by HPLC (35% H20/MeCN through a Kromasil C-18 250× 20 mm column, 12 mL/min) to provide 6.2 mg (10%) of the faster eluting Z isomer and 1.4 mg (2%) of the E isomer. Z isomer: high-resolution mass spectrum (FAB) m/z 1008.5790 [(M+Na)+, calcd for C, 53; H, 83; N, 3O; 14; Na, 1008.5768;]. E isomer: high-resolution mass spectrum (FAB) m/z 1008.5753 [(M+Na)+, calcd for C, 53; H, 83; N, 3O; 14; Na, 1008.5768;].

2. Assay of Binding of Rapamycin C24 Derivatives to FKBP

Affinities of rapamycin C24 analogs for FKBP were determined using a competitive assay based on fluorescence polarization (FP). A fluorescein-labelled FK506 probe (AP1491) was synthesized, and the increase in the polarization of its fluorescence used as a direct readout of % bound probe in an equilibrium binding experiment containing sub-saturating FKBP and variable amounts of rapamycin analog as competitor.

Synthesis of Fluoresceinated FK506 Probe (AP1491)

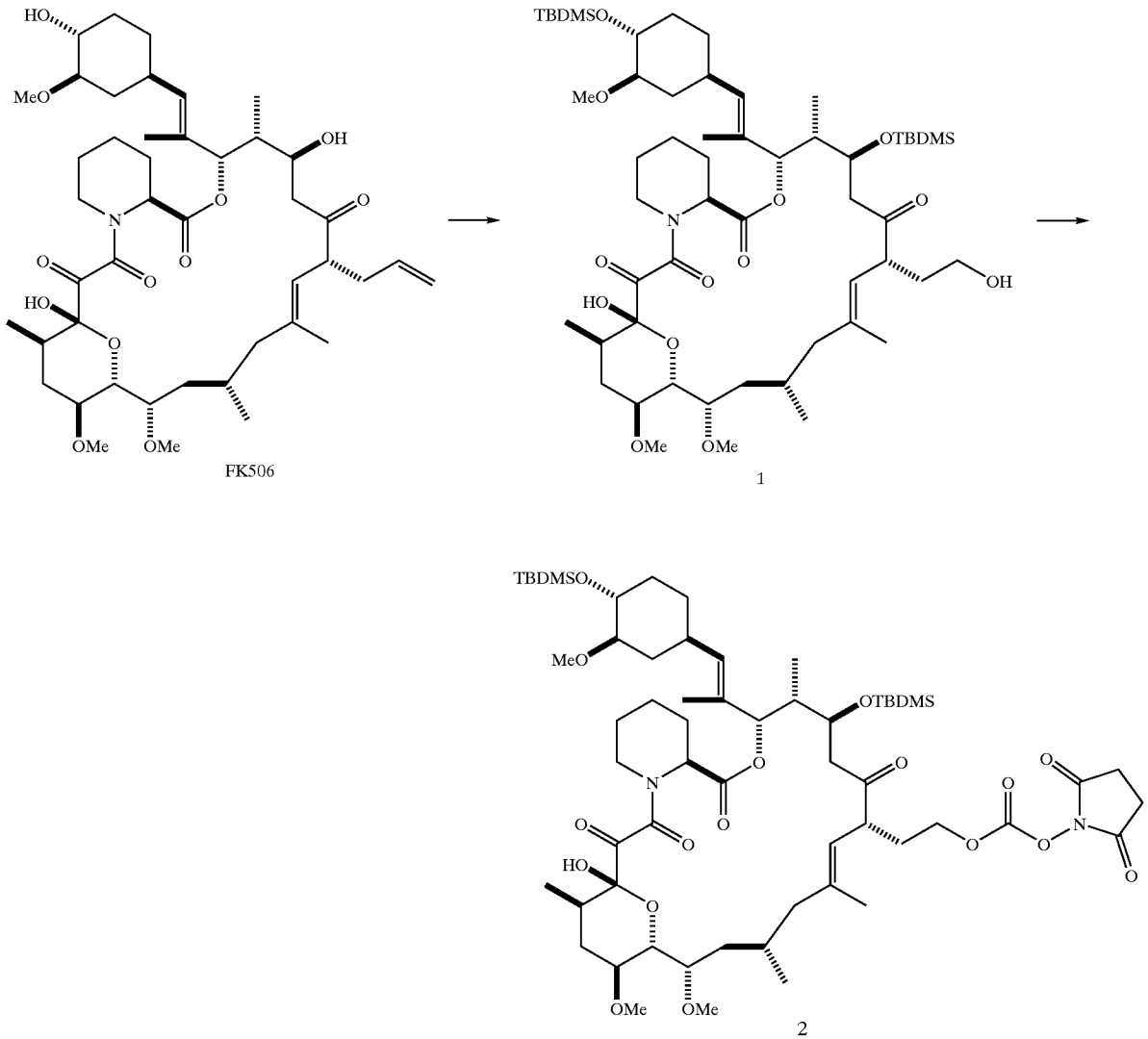

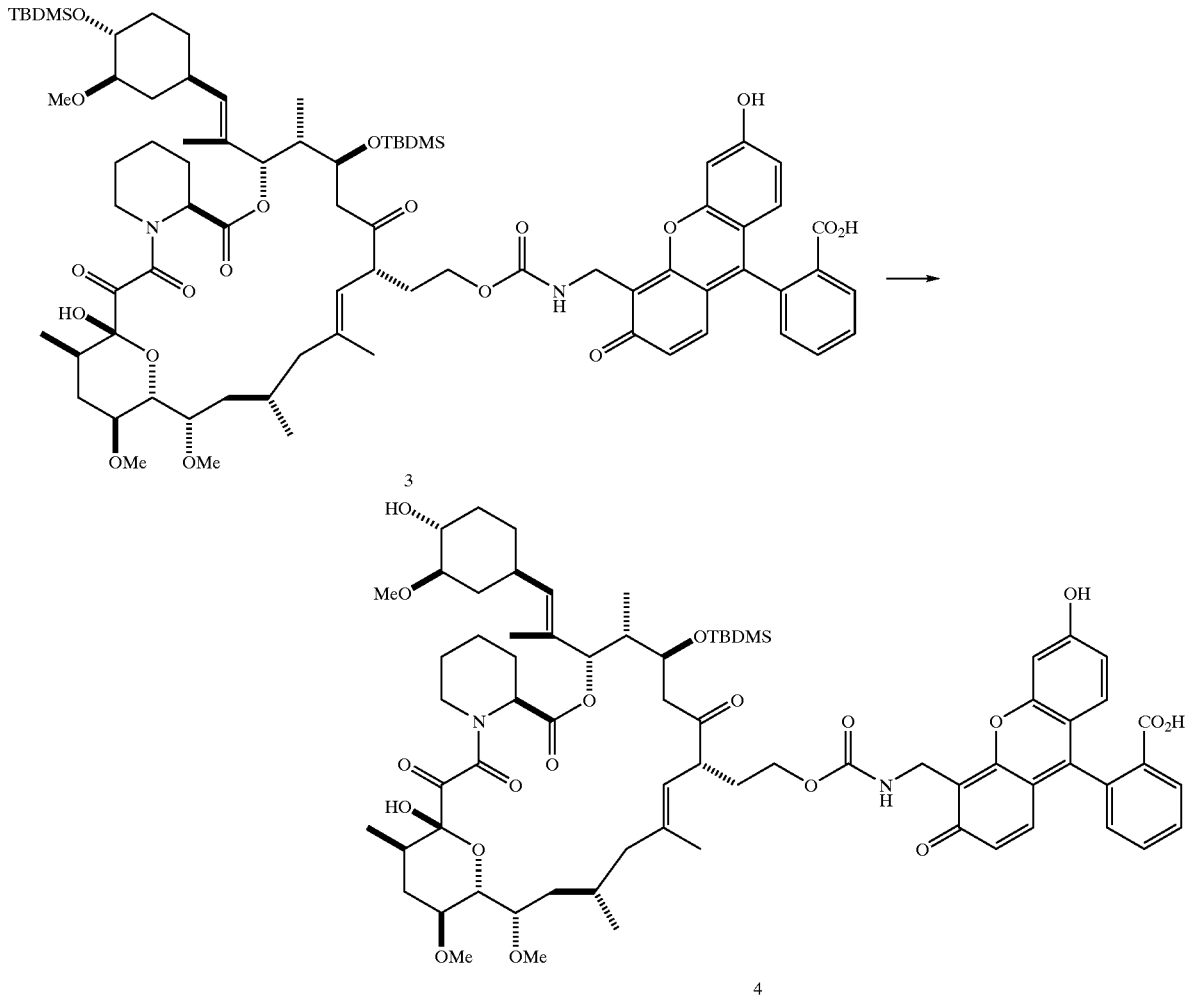

Example 2.1

24,32-Bis(tert-Butyldimethylsilyl)ether of FK506 tert-Butyldimethylsilyl trifluoromethanesulfonate (108 µL, 470 µmol) was added dropwise to a stirred solution of FK506 (103 mg, 128 µmol) and 2,6-lutidine (89.5 µL, 768 µmol) in dichloromethane (3 mL) at 0° C. The resulting solution was stirred at 0° C. for 2 h, and then treated with MeOH (0.5 mL) and ether (15 mL). The mixture was washed with 10% aqueous NaHCO3 (3 mL) and brine (3 mL). The organic layer was decanted, dried over anhydrous Na2SO4, filtered, and concentrated to a yellow oil. Column chromatography (silica-gel, hexanes-EtOAc 3:1) gave the title compound as a colorless oil (104 mg).

Example 2.2

Intermediate 1

To a solution of 24,32-bis(tert-butyldimethylsilyl)ether of FK506 (100 mg, 97 µmol) in THF (2.5 mL) was added morpholine N-oxide (68 mg, 580 µmol), followed by water (60 µL), and a 4% aqueous solution of osmium tetroxide (123 µL, 20 µmol). The resulting mixture was stirred at room temperature for 4.5 h. It was then treated with 50% aqueous MeOH (1.5 mL) and sodium periodate (207 mg, 970 µmol), and the suspension stirred for an additional 1 h. The mixture was diluted with ether (10 mL) and washed with saturated aqueous NaHCO3 (2×4 mL). The organic layer was decanted, dried over anhydrous sodium sulfate containing a small amount of sodium sulfite, filtered, and concentrated. The residue was dissolved in anhydrous THF (2.8 mL), cooled to −78° C. under nitrogen, and treated with a 0.5 M solution of lithium tris [(3-ethyl-3-pentyl)oxy]aluminum hydride in THF (282 µL). The resulting solution was stirred at −78° C. for 1.75 h, and then quenched by addition of ether (6 mL) and saturated ammonium chloride solution (250 µL). The mixture was allowed to warm up to room temperature and treated with anhydrous sodium sulfate. Filtration and concentration under reduced pressure afforded a pale yellow oil (97 mg), which was purified by column chromatography (silica-gel, hexanes-EtOAc 3:1) to afford 1 as a colorless oil.

Example 2.3

Intermediate 2

A solution of the above alcohol (300 mg, 290 µmol) in acetonitrile (10 mL) was treated with 2,6-lutidine (338 µL, 2.9 mmol) and N,N'-disuccinimidylcarbonate (371 mg, 1.45 mmol). The resulting suspension was stirred at room temperature for 14.5 h, and then concentrated under reduced pressure. The residue was chromatographed (silica-gel, hexanes-EtOAc 2:1 to 100% EtOAc gradient) to afford the mixed carbonate 2 as a pale yellow oil (127 mg).

Example 2.4

Intermediate 3

A solution of the above carbonate (30 mg, 26 μmol) and triethylamine (36 μL, 260 μmol) in acetonitrile (1 mL) was treated with 4'-(aminomethyl)fluorescein (13.5 mg, 34 μmol). The resulting bright orange suspension was stirred at room temperature for 1 h, and then concentrated under reduced pressure. The residue was chromatographed (silica-gel, hexanes-EtOAc 1:1 to 100% EtOAc to EtOAc-MeOH 1:1 gradient) to give 3 (20.5 mg) as a bright yellow solid.

Example 2.5

Compound 4

A solution of bis-silyl ether 3 (35 mg, 25 μmol) in acetonitrile (2 mL) was treated with 48% (w/w) HF in water (250 μL). The resulting mixture was stirred at room temperature for 5.5 h. It was then diluted with dichloromethane (10 mL) and washed with water (2×2 mL). The organic layer was decanted, dried over anhydrous sodium sulfate, and concentrated under reduced pressure. The residue was chromatographed (silica-gel, 100% EtOAc) to afford 4 (13 mg) as a bright yellow solid.

Example 2.6

Determination of Binding Affinities (IC50s) of Rapalogs Using FP

Serial 10-fold dilutions of each analog were prepared in 100% ethanol in glass vials and stored on ice. All other manipulations were performed at room temperature. A stock of recombinant pure FKBP (purified by standard methods, see eg. Wiederrecht, G. et al. 1992. J. Biol. Chem. 267, 21753–21760) was diluted to approximately 3 nM in 50 mM potassium phosphate pH 7.8/150 mM NaCl/100 μg/ml bovine gamma globulin ("FP buffer": prepared using only low-fluorescence reagents from Panvera) and 98 μl aliquots transferred to wells of a Dynatech micro-fluor black 96-well fluorescence plate. 2.0 μl samples of the rapamycin analogs were then transferred in duplicate to the wells with mixing. Finally, a probe solution was prepared containing 10 nM AP1491 in 0.1% ethanol/FP buffer, and 100 μl added to each well with mixing. Duplicate control wells contained ethanol instead of rapamycin analog (for 100% probe binding) or ethanol instead of rapamycin analog and FP buffer instead of FKBP (0% binding).

The plates were stored covered in the dark for approximately 30 min to permit equilibration and then the fluorescence polarization of the sample in each well read on a Jolley FPM-2 FP plate reader (Jolley Consulting and Research, Inc., Grayslake, Ill.) in accordance with the manufacturer's recommendations. The mean polarization (mP units) for each competitor concentration was usually converted to % total binding by reference to the control values and plotted (y) vs. log molar final concentration of competitor (x). Non-linear least square analysis was used to fit the curve and extract the IC50 using the following equation:

$$y = M1 + (M4 - M1)/(1 + \exp(M2*(M3 - x)))$$

where M3 is the IC50. For incomplete curves the IC50 was determined by interpolation. Rapamycin and C14-desoxo-rapamycin were included as controls in each case (C14-desoxo-rapamycin was prepared as described by Luengo, J. I. et al. 1994 Tet Lett. 35, 6469–6472).

Example 2.7

Results of Binding Analysis of Rapamycin C24 Oximes

Affinities are reported as IC50s and as fold loss in affinity (=IC50/IC50 of rapamycin). (Comparative binding data of C24 rapalogs vs rapamycin and desoxo-rapamycin towards human FKBP12 are plotted in PCT/US86/09848.)

TABLE 4

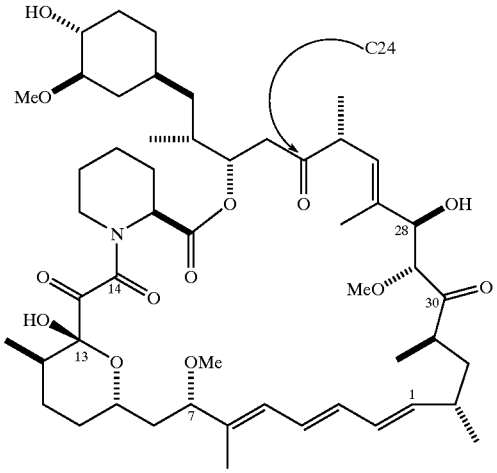

| cmpd | C24 | isomer | FKBP wt FP binding assay IC50 (nM) | fold loss in affinity (vs rapamycin) |
|---|---|---|---|---|
| rapamycin | | | 2.3 | (1) |
| C14 desoxo | | | 63.3 | 27.5 |
| 17 | | Z (major) | 618 | 269 |
| 18 | | E (minor) | 59.1 | 25.7 |
| 5 | | Z (major) | 1416 | 616 |
| 6 | | E (minor) | 438 | 190 |

TABLE 4-continued
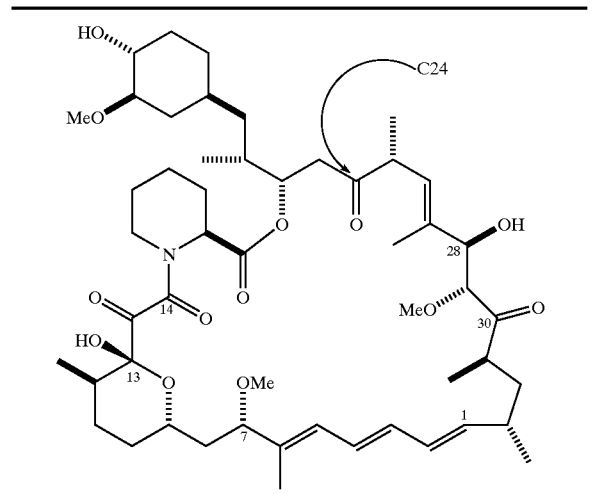
| cmpd | C24 | isomer | FKBP wt FP binding assay IC50 (nM) | fold loss in affinity (vs rapamycin) |
|---|---|---|---|---|
| 7 |  | Z (major) | 2960 | 1287 |
| 8 |  | E (minor) | 1664 | 723 |
| 9 | 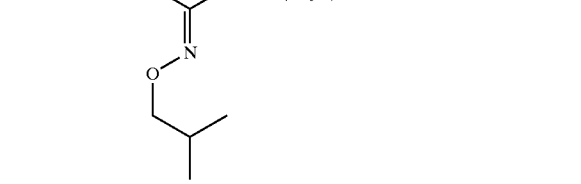 | Z (major) | >30000 | >13043 |
| 10 | 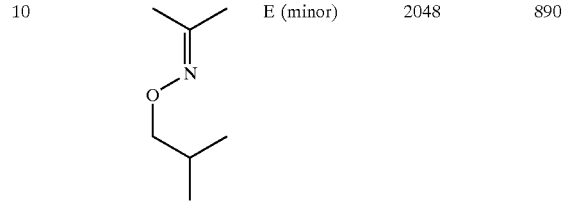 | E (minor) | 2048 | 890 |
| 19 | 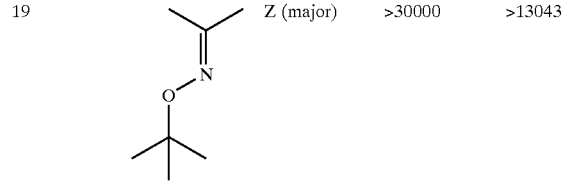 | Z (major) | >30000 | >13043 |
TABLE 4-continued
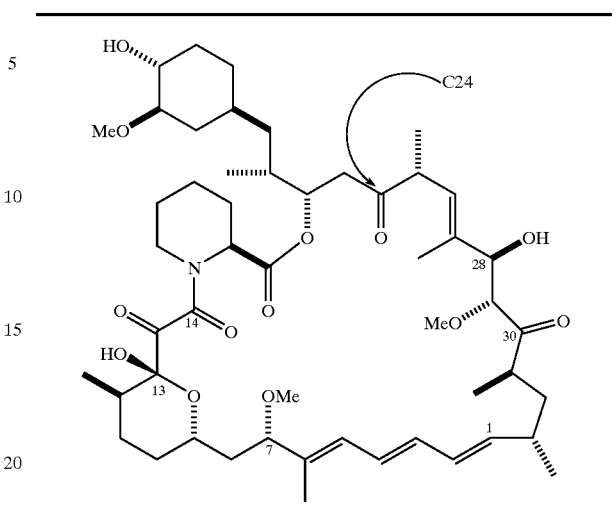
| cmpd | C24 | isomer | FKBP wt FP binding assay IC50 (nM) | fold loss in affinity (vs rapamycin) |
|---|---|---|---|---|
| 20 | 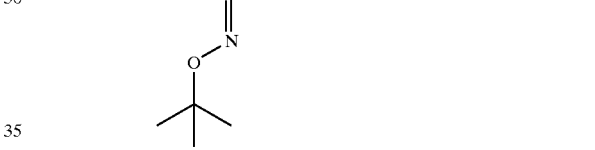 | E (minor) | 2406 | 1046 |
| 11 | 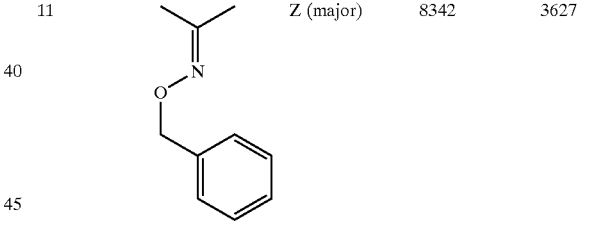 | Z (major) | 8342 | 3627 |
| 12 | 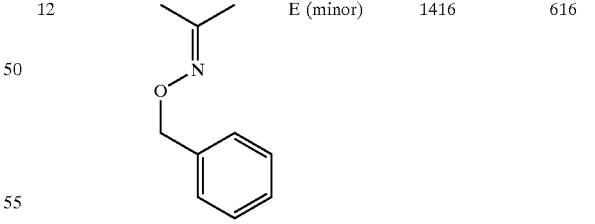 | E (minor) | 1416 | 616 |
| 13 | 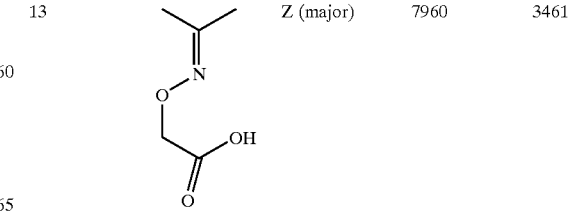 | Z (major) | 7960 | 3461 |

TABLE 4-continued

[Structure of rapamycin analog with C24 position indicated, showing HO, MeO, piperidine ring, macrolactone with C13, C14, C28, C30, OMe, OH substituents]

| cmpd | C24 | isomer | FKBP wt FP binding assay IC50 (nM) | fold loss in affinity (vs rapamycin) |
|---|---|---|---|---|
| 14 | [=N-O-CH2-C(=O)-OH] | E (minor) | 2351 | 1022 |
| 15 | [=N-O-CH2-C(=O)-NH2] | Z (major) | 1151 | 500 |
| 16 | [=N-O-CH2-C(=O)-NH2] | E (minor) | 204 | 88.7 |

3. Synthesis of C7 Rapalogs and Assay of Binding of C7 Rapalog-FKBP Complexes to FRAP A series of C7 rapalogs containing various C7 substituents selected from branched and unbranched alkoxy, arylalkyloxy, —NHCO—Oalkyl, —NHSO$_2$alkyl and substituted aryl and heteroaryl moieties was synthesized using chemistry generally as described in the literature except as noetd (see e.g., Luengo et al. 1995. Chemistry and Biology 2, 471–481, and the references cited in Table II for additional background). See also the table which follows.

Example 3.1

Compounds 27, 28—($R^{C7}$=Et) are synthesized as described in Luengo et al, Chemistry & Biology July 1995, 2:471–481.

Example 3.2

Compound 29—($R^{C7}$=iPr) A solution of rapamycin (60 mg, 0.066 mmol) in 2-propanol (3 mL) at room temperature was treated with para-toluenesulfonic acid (75 mg, 0.394 mmol) and allowed to stir for 4 h. After this time the reaction was poured onto a biphasic solution of saturated aqueous NaHCO$_3$ (20 mL) and EtOAc (30 mL). The organic layer was washed with additional solution of saturated aqueous NaHCO$_3$ (2×20 mL) followed by a saturated aqueous solution of NaCl (2×10 mL) then dried over Na$_2$SO$_4$, filtered, evaporated. The resulting material was purified by HPLC on a Kromasil C-18 column (20×250 mm) at 55 C. using 65% acetonitrile/water as eluant to afford AP1700 (25 mg). MS(FAB): (M+Na)$^+$ calcd: 964.5762, found: 964.5753.

Example 3.3

Compound 30—($R^{C7}$=benzyl) is synthesized as described in Chemistry & Biology July 1995, 2:471–481.

Example 3.4

Compounds 31, 32—($R^{C7}$=—NH—CO—Ome) may be synthesized as described in Chemistry & Biology July 1995, 2:471–481.

Example 3.5

Compound 33—($R^{C7}$=—NH—SO$_2$—Me) A solution of rapamycin (75 mg, 0.082 mmol) and methanesufonamide (312 mg, 3.282 mmol) in dichloromethane (3 mL) at −40° C. was treated dropwise with trifluoroacetic acid (126 μL, 1.636 mmol) and allowed to stir for 3 h. After this time the reaction was poured onto a biphasic solution of saturated aqueous

[Structure of rapamycin analog showing positions with $R^{C7a}$ and $R^{C7b}$ substituents at C7]

| # | $R^{C7a}$ | $R^{C7b}$ |
|---|---|---|
| rapamycin | —OMe | H |
| C14-desoxo rapamycin | —OMe | H |
| 27 | —OEt | H |
| 28 | H | —OEt |
| 29 | —O-iPr | H |
| 30 | —O-benzyl | H |
| 32 | —NH—(C=O)—OMe | H |
| 31 | H | —NH—(C=O)—OMe |
| 33 | —NH—SO$_2$Me | H |

-continued

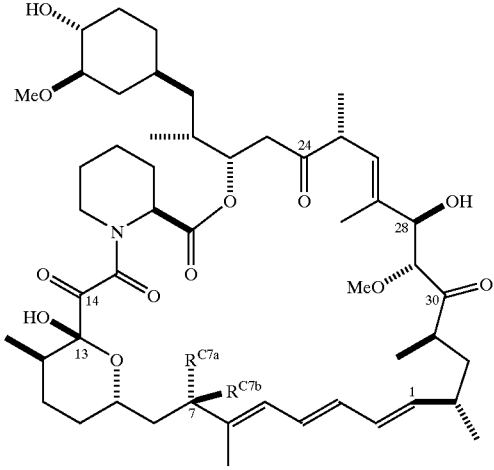

| # | $R^{C7a}$ | $R^{C7b}$ |
|---|---|---|
| 34 | 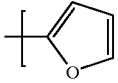 | H |
| 35 | H | 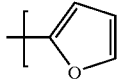 |
| 36 | 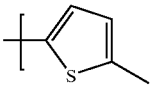 | H |
| 37 | H | 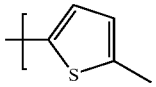 |
| 38 | 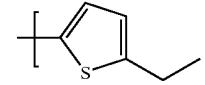 | H |
| 39 | H | 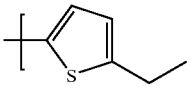 |
| 41 | 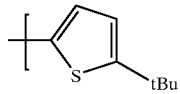 | H |
| 40 | H | 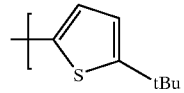 |
| 42 | -o,p-dimethoxyphenyl | H |
| 43 | H | -o,p-dimethoxyphenyl |
| 44 | 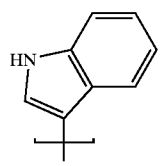 | H |

-continued

| # | $R^{C7a}$ | $R^{C7b}$ |
|---|---|---|
| 45 | H | (indole) |
| 46 | -o,p-diethoxyphenyl | H |
| 47 | (3-methylthiophene) | H |
| 48 | (pyrrole) | H |
| 49 | -2,4,6-trimethoxyphenyl | H |
| 50 | H | -2,4,6-trimethoxyphenyl |
| 51 | —NH—(C=O)—OEt | H |
| 52 | H | —NH—(C=O)—OEt |

NaHCO$_3$ (20 mL) and EtOAc (10 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc: MeOH, 200:50:42.5:7.5). The resulting semipurified material was purified by HPLC on a Kromasil C-18 column (20×250 mm) at 55 C. using 65% acetonitrile/water as eluant to afford AP1705 (24 mg). MS(FAB): (M+Na)$^+$ calcd: 999.5246, found: 999.5246.

Example 3.6

Compounds 34, 35—($R^{C7}$=furanyl) These compounds may be synthesized as described in Chemistry & Biology July 1995, 2:471–481.

Example 3.7

Compounds 36, 37—($R^{C7}$=methylthiophene) These compounds may be synthesized as described in J. Org. Chem 1994, 59, 6512–6513.

Example 3.8

Compounds 39, 38—($R^{C7}$=ethylthiophene) A solution of rapamycin (50 mg, 0.055 mmol) and 2-ethylthiophene (248 µL, 2.188 mmol) in dichloromethane (1.5 ML) at −40° C. was treated dropwise with trifluoroacetic acid (84 uL, 1.094 mmol) and allowed to stir for 3 h. After this time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered, evaporated, and flash chromatographed on a silica gel (MeOH:dichloromethane, 2:98 then 5:95). The resulting semipurified material was purified by HPLC on a Kromasil C-18 column (20×250 mm) at 55 C. using 80% acetonitrile/water as eluant to afford AP1858 (6 mg) and AP1859 (28 mg). MS(ES+): (M+NH$_4$)$^+$1016; MS(ES−): (M−H)$^-$992.

Example 3.9

Compounds 40, 41—($R^{C7}$=tertbutyl thiophene) A solution of rapamycin (50 mg, 0.055 mmol) and 2-tert-butylylthiophene (276 mg, 2.188 mmol) in dichloromethane (1.5 mL) at −40° C. was treated dropwise with trifluoroacetic acid (84 µL, 1.094 mmol) and allowed to stir for 3 h. After this time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered. evaporated, and flash chromatographed on a silica gel (MeOH:dichloromethane, 2:98 then 5:95). The resulting semipurified material was purified by HPLC on a Kromasil C-18 column (20×250 mm) at 55 C. using 80% acetonitrile/water as eluant to afford AP1856 (4 mg) and AP1857 (14 mg). MS(ES+): (M+Na)$^+$1045; MS(ES−): (M−H)$^-$1021.

Example 3.10

Compounds 43, 42—($R^{C7}$=o,p-dimethoxyphenyl) These compounds may be found in Chemistry & Biology July 1995, 2:471–481.

Example 3.11

Compounds 44, 45—($R^{C7}$=indolyl) A solution of rapamycin (50 mg, 0.055 mmol) and indole (64 mg, 0.547 mmol) in dichloromethane (2.0 mL) at −40° C. was treated dropwise with trifluoroacetic acid (84 µL, 1.094 mmol) and allowed to stir for 3 h. After this time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc: MeOH, 200:50:42.5:7.5). The resulting semipurified material was purified by HPLC on a Kromasil C-18 column (20×250 mm) using 65% acetonitrile/water as eluant for AP1701 (12 mg) and AP1702 (7.6 mg). MS(FAB): (M+Na)$^+$ calcd: 1021.5765, found: 1021.5788 (AP1701) and 1021.5797 (AP1702)

Example 3.12

Compound 46—($R^{C7}$=o,p-diethoxyphenyl) A solution of rapamycin (108 mg, 0.118 mmol) and 1,3-diethoxybenzene (783 mg, 4.72 mmol) in dichloromethane (2.0 mL) at −40° C. was treated dropwise with trifluoroacetic acid (154 µL, 2.01 mmol) and allowed to stir for 3 h. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 200:50:42.5:7.5). The resulting material was purified by HPLC on a Rainin silica column (20×250 mm) using (dichloromethane:hexane:EtOAc:MeOH, 210:65:65:10) as eluant for AP20808 (20 mg). MS(ES+): (M+Na)$^+$1065.95.

Example 3.13

Compound 47—($R^{C7}$=methylthiophene) A solution of rapamycin (105 mg, 0.115 mmol) and 3-methylthiophene (445 µL, 4.60 mmol) in dichloromethane (2.0 mL) at −40° C. was treated dropwise with trifluoroacetic acid (150 µL, 1.96 mmol) and allowed to stir for 3 h. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 200:50:42.5:7.5). The resulting material was purified by HPLC on a Rainin silica column (20×250 mm) using (dichloromethane:hexane:EtOAc:MeOH, 210:65:65:10) as eluant for AP20809 (60 mg). MS(ES+): (M+Na)$^+$1002.96.

Example 3.14

Compound 48—($R^{C7}$=N-methylpyrrole) A solution of rapamycin (51 mg, 0.056 mmol) and N-methylpyrrole (198 µL 2.23 mmol) in dichloromethane (2.0 mL) at 0° C. was treated with zinc chloride (76 mg, 0.557 mmol) and allowed to warm to rt overnight. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 100:150:150:10). The resulting material was purified by HPLC on a Rainin Si column (20×250 mm) using (dichloromethane:hexane:EtOAc:MeOH, 210:65:65:10) as eluant for AP20810 (10 mg). MS(ES+): (M+NH4)$^+$981.05; MS(ES−): (M−H)$^-$961.69.

The C7 rapalogs were characterized by exact mass spec and NMR.

Example 3.15

FP assay of FKBP binding affinity of C7 rapalogs

The affinity of a variety of the C7 rapalogs for FKBP was assayed as described for C24 rapalogs above, using competitive FP. Rapamycin and C14-desoxo-rapamycin (prepared as described by Luengo et al. 1994. Tetrahedron Lett. 35, 6469–6472) were included as controls.

Affinities are reported below as IC50s and fold loss in affinity (=IC50/IC50 of rapamycin). See "Illustrative C7 Rapalogs" Table below. These data indicate that these large C7 substituents do not necessarily cause large reductions in the affinity of the rapalogs for human FKBP.

| Compound | FKBPwt FP binding assay IC50 (nM) | fold loss in affinity (cf rapamycin) |
|---|---|---|
| rapamycin | 2.3 | (1) |
| C14 desoxorap | 34 | 15 |
| 27 | 2.6 | 1.1 |
| 28 | 3.7 | 1.6 |
| 29 | 2.2 | 1.0 |
| 30 | 12 | 5.2 |
| 32 | 4.3 | 1.9 |
| 31 | 2.6 | 1.1 |
| 33 | 2.5 | 1.1 |
| 34 | 28 | 12 |
| 35 | 29 | 13 |
| 36 | 3.7 | 1.6 |
| 37 | 4.3 | 1.9 |
| 38 | 2.5 | 1.1 |
| 39 | 2.4 | 1.0 |
| 41 | 2.9 | 1.3 |
| 40 | 3.4 | 1.5 |
| 42 | 2.2 | 1.0 |
| 43 | 20 | 8.7 |
| 44 | 7.8 | 3.3 |
| 45 | 5.9 | 2.6 |

Example 4.1

Preparation of Rapalogs Modified at $R^{C24}$ and $R^{C30}$: 24(S),30 (S)-tetrahydrorapamycin (53)

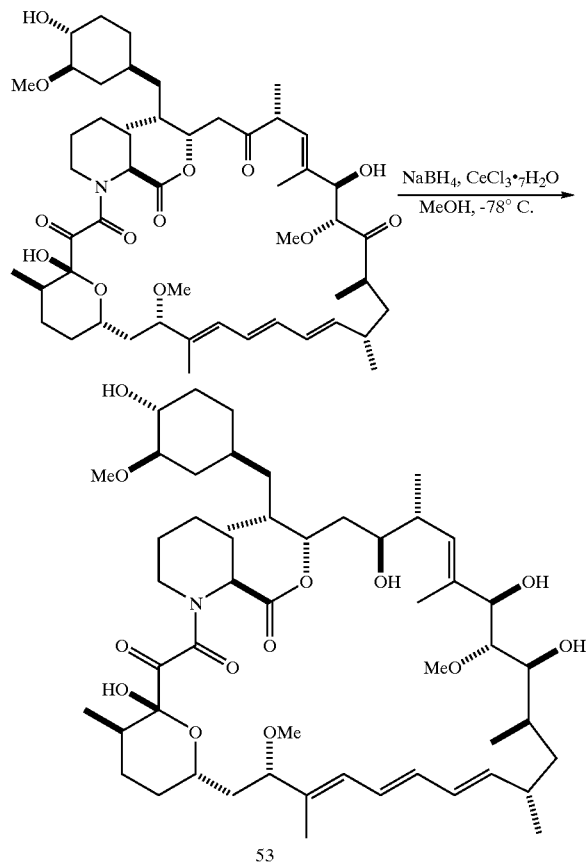

Rapamycin (46 mg, 0.050 mmol) was dissolved in 2.0 mL of methanol, cooled to −78° C., and cerium (III) chloride heptahydrate (46 mg, 0.123 mmol) was added. The solution was stirred for 0.25 h., then sodium borohydride (7.6 mg, 0.20 mmol) was added. After 0.5 h, the reaction mixture was partitioned between ethyl acetate (15 mL) and 5% aqueous hydrochloric acid (2 mL). The organic phase was washed with water (2 mL) and brine (1 mL), dried over anhydrous magnesium sulfate, filtered, and concentrated. Flash chromatography (silica gel, 15:75:50:200 methanol:ethyl acetate:hexane:dichloromehane) yielded 35 mg (76%) of the desired product as a white foam. Mass spectral data: (FS+/NaCl/NH3) mlz 942.21 (M+Na)+, 935.83 (M+NH4)+; (ES−/NaCl) m/z 963.04 (M+Cl)−, 917.34 (M−H)− lit. ref. Luengo, J. I.: Rozamus, L. W., Holt, D. A. Tetrahedron Lett. 1994, 35, 6469–6472.

Example 5.1

Preparation of Rapalogs Modified at C24, C30 and C7

24(S). 30(S)-tetrahydrorapamycin (53), prepared as in Example 4, may be modified at C7 using approaches illustrated in the prior C7 rapalog examples. For example:

7(S)-(2′,4′-dimethoxy)benzyl-7-demethoxy-24(S), 30(S)-tetrahydro-rapamycin

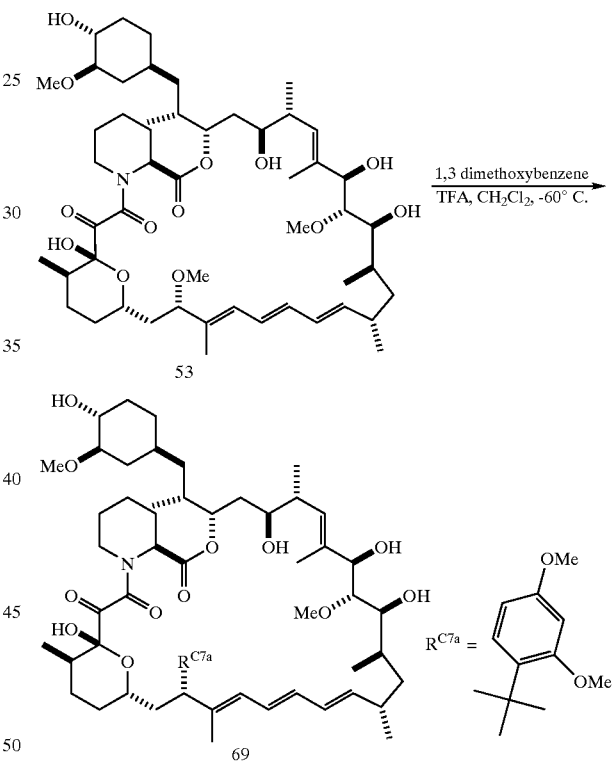

24(S), 30(S)-tetrahydro-rapamycin (20 mg, 0.022 mmol) was dissolved in dichloromethane (1.0 mL). 1,3-dimethoxybenzene (0.20 mL, 1.5 mmol) was added, and the solution was cooled to −60° C. Trifluoroacetic acid (0.030 mL, 0.39 mmol) was added, and the reaction mixture was stirred for 1 h at −60° C., then partitioned between ethyl acetate (10 mL) and saturated aqueous sodium bicarbonate (1 mL). The organic phase was washed with water (2 mL) and brine (1 mL), dried over anhydrous magnesium sulfate, filtered, and concentrated. Flash chromatography (silica gel, 15:75:50:200 methanol:ethyl acetate:hexane:dichloromehane) yielded 8 mg (35%) of the desired product as a white solid. Mass spectral data: (ES+/NaCl/NH3) m/z 1046.96 (M+Na)+, 1042.15 (M+NH4)+; (ES−/NaCl) m/z 1069.09 (M+Cl)− lit. ref. Luengo, J. I.;

Konialian-Beck, A.; Rozamus, L. W.; Holt, D. A. J. Org. Chem. 1994, 59, 6512–6513.

By analogous means, one may produce 24(S), 30(S)-tetrahydro rapamycins bearing other C7 substituents as described elsewhere herein, e.g., containing alternatively substituted aryl groups, heteroaryl, —O-aliphatic groups, thioethers, or any of the other types of moieties designated previously for $R^{C7a}$ or $R^{C7b}$. These compounds may be obtained by reduction at C24 and C30 of the appropriate C7 rapalog, or by transformation at C7 of the appropriate C24, C30-tetrahydro rapalog. Illustrative examples follow.

Rapalogs modified at C24, C30 and C7 may also be differ from rapamycin at the various positions discussed herein, e.g. with respect to one or more of $R^{C13}$, $R^{C43}$, $R^{C28}$, $R^{C29}$, $R^4$, "a", etc. By way of example, starting with 13-F-rapamycin in place of rapamycin yields the 13-fluoro analogs of compounds 53–79.

Example 5.2

Compounds 54, 55—($R^{C7}$=Et) are synthesized as described in Example 4.1, but substituting Compounds 27 and 28, respectively, for rapamycin.

Example 5.3

Compound 56—($R^{C7}$=iPr) is synthesized as described in Example 4.1, but substituting Compound 29 for rapamycin.

Example 5.4

Compound 57—($R^{C7}$=benzyl) is synthesized as described in Example 4.1, but substituting Compound 30 for rapamycin.

Example 5.5

Compounds 58, 59—($R^{C7}$=—NH—CO—Ome) are synthesized as described in Example 4.1, but substituting Compounds 32 and 31, respectively, for rapamycin.

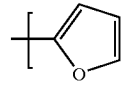

| # | $R^{C7a}$ | $R^{C7b}$ |
|---|---|---|
| 53 | —OMe | H |
| 54 | —OEt | H |
| 55 | H | —OEt |
| 56 | —O-iPr | H |
| 57 | —O-benzyl | H |

-continued

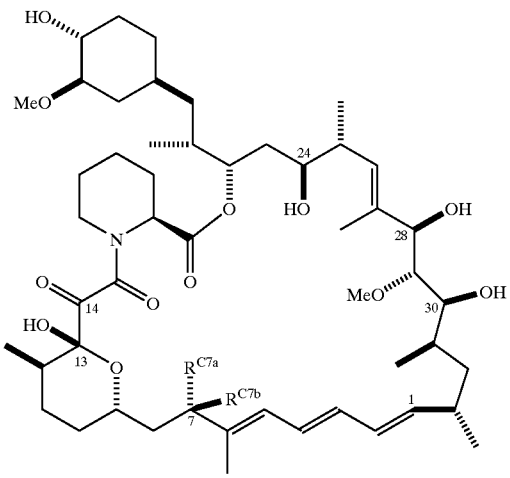

| # | $R^{C7a}$ | $R^{C7b}$ |
|---|---|---|
| 58 | —NH—(C=O)—OMe | H |
| 59 | H | —NH—(C=O)—OMe |
| 60 | —NH—SO$_2$Me | H |
| 61 | [furan] | H |
| 62 | H | [furan] |
| 63 | [methylthiophene] | H |
| 64 | H | [methylthiophene] |
| 65 | [ethylthiophene] | H |
| 66 | H | [ethylthiophene] |
| 67 | [tBu-thiophene] | H |
| 68 | H | [tBu-thiophene] |
| 69 | -o,p-(MeO)$_2$phenyl | H |
| 70 | H | -o,p-(MeO)$_2$phenyl |

-continued

| # | $R^{C7a}$ | $R^{C7b}$ |
|---|---|---|
| 71 | (3-indolyl) | H |
| 72 | H | (3-indolyl) |
| 73 | -o,p-diethoxyphenyl | H |
| 74 | (3-methylthiophen-2-yl) | H |
| 75 | (pyrrol-2-yl) | H |
| 76 | -2,4,6-(MeO)$_3$phenyl | H |
| 77 | H | -2,4,6-(MeO)$_3$phenyl |
| 78 | —NH—(C=O)—OEt | H |
| 79 | H | —NH—(C=O)—OEt |

Example 5.6

Compound 60—($R^{C7}$=—NH—SO2-Me) is synthesized as described in Example 4.1, but substituting Compound 31 for rapamycin Example 5.7

Compounds 61 and 62—($R^{C7}$=furanyl) are synthesized as described in Example 4.1, but substituting Compounds 34 and 35, respectively, for rapamycin.

Example 5.8

Compounds 63, 64—($R^{C7}$=methylthiophene) are synthesized as described in Example 4.1, but substituting Compounds 36 and 37, respectively, for rapamycin.

Example 5.9

Compounds 65, 66—($R^{C7}$=ethylthiophene) are synthesized as described in Example 4.1, but substituting Compounds 38 and 39, respectively, for rapamycin.

Example 5.10

Compounds 67, 68—($R^{C7}$=tertbutyl thiophene) are synthesized as described in Example 4.1, but substituting Compounds 41 and 40, respectively, for rapamycin.

Example 5.11

Compounds 69, 70—($R^{C7}$=o,p-dimethoxyphenyl) are synthesized as described in Example 4.1, but substituting Compounds 43 and 42, respectively, for rapamycin.

Example 5.12

Compounds 71, 72—($R^{C7}$=indolyl) are synthesized as described in Example 4.1, but substituting Compounds 45 and 44, respectively, for rapamycin.

Example 5.13

Compound 73—($R^{C7}$=o,p-diethoxyphenyl) is synthesized as described in Example 4.1, but substituting Compound 46 for rapamycin.

Example 5.14

Compound 74—($R^{C7}$=methylthiophene) is synthesized as described in Example 4.1, but substituting Compound 47 for rapamycin.

Example 5.15

Compound 75—($R^{C7}$=N-methylpyrrole) is synthesized as described in Example 4.1, but substituting Compound 4 for rapamycin.

Example 5.16

Compound 75, 76—($R^{C7}$=2,4,6-trimethoxyphenyl) is synthesized as described in Example 5.1, but substituting 1,3,5-trimethoxybenzene for 1,3-dimethoxybenzene.

6. Preparation of Fluoro-Rapalogs

Example 6.1

A new class of rapalogs, C13-Fluoro-rapalogs, may be prepared by the following route:

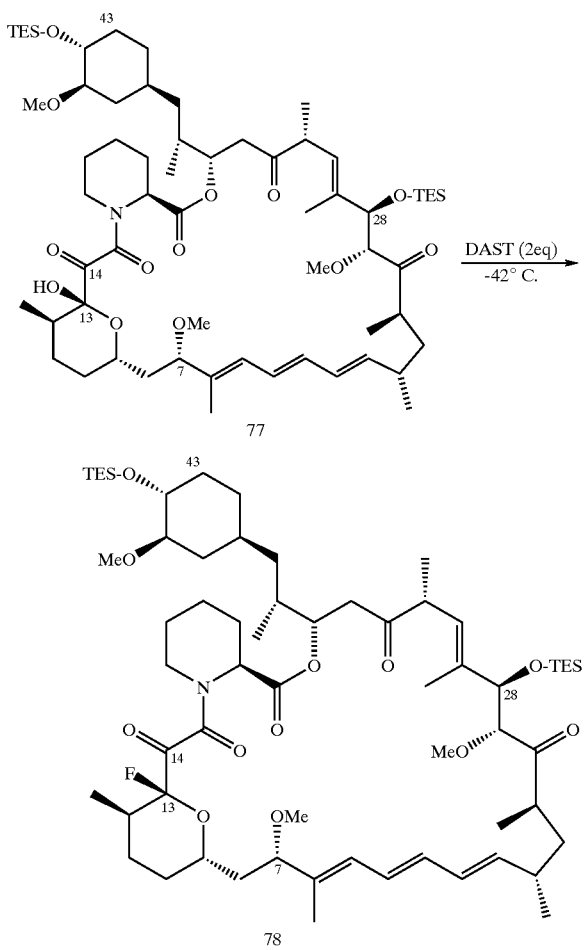

77

78

In this example, the hydroxyl moieties at positions 28 and 43 are protected prior to treatment with DAST. We have used bis-triethylsilyl (as shown above) and bis-triisopropylsilyl protecting groups. Various alternative protecting groups may be used, based on user preference or convenience and in consideration of the reaction conditions of subsequent transformations prior to or concurrent with removal of protecting groups. The protected compound is then treated with the DAST reagent to introduce the 13-fluoro substituent. The DAST reaction may be conducted, e.g., at −42° C. as shown, or at 0° C.

13-Fluoro rapamycin may then be modified at position 7 as desired to produce the family of 13-fluoro C7-rapalogs bearing any of the variety of moieties designated previously for $R^{C7a}$ or $R^{C7b}$ For instance, the 7-(o,p-dimethoxy)-13-fluoro-rapalogs (96 and 97) may be prepared (and separately recovered if desired) by transformation of 78 at C7 followed by removal of protecting groups, or, as shown below, by removal of protecting groups from 78 followed by transformation at C7.

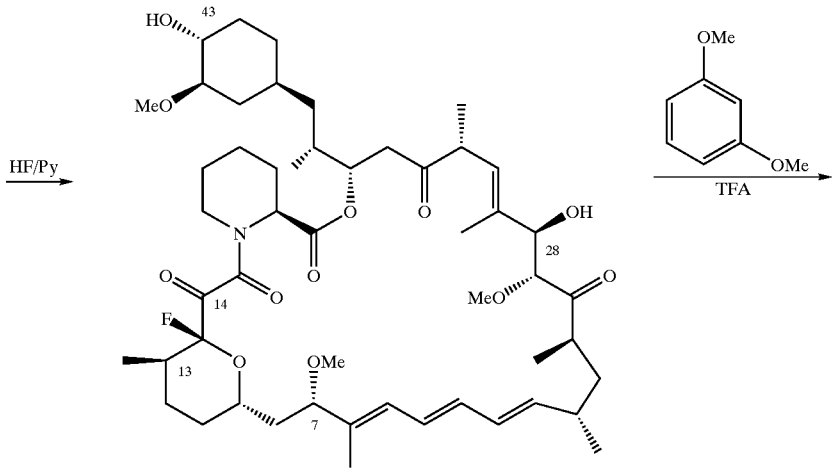

79

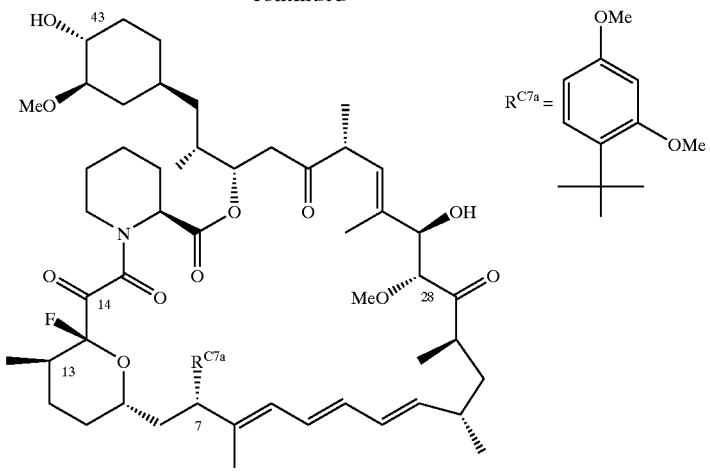

80

One may subject 13-F-rapamycin, instead of rapamycin, to various other chemical transformations such as are disclosed or referred to herein, including, for instance, fluorination at C28, reduction at C24 and C30, fluorination at C24 and C30, modification at C-43, etc., in addition to or as an alternative to modification at C7, in order to obtain the corresponding 13-F analog.

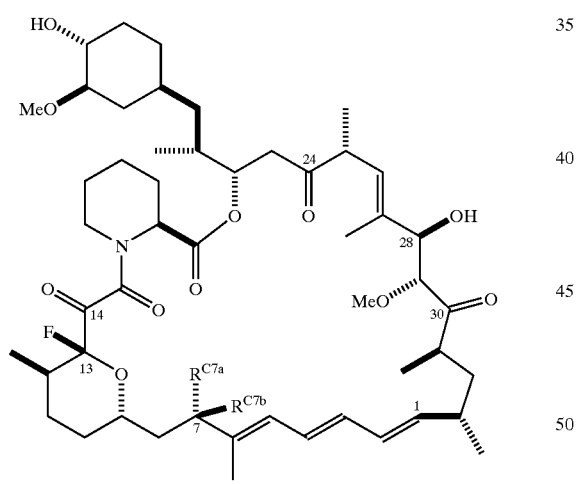

| # | $R^{C7a}$ | $R^{C7b}$ |
|---|---|---|
| 81 | —OEt | H |
| 82 | H | —OEt |
| 83 | —O-iPr | H |
| 84 | —O-benzyl | H |
| 85 | —NH—(C=O)—OMe | H |
| 86 | H | —NH—(C=O)—OMe |
| 87 | —NH—SO$_2$Me | H |
| 88 | 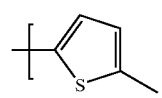 | H |

-continued

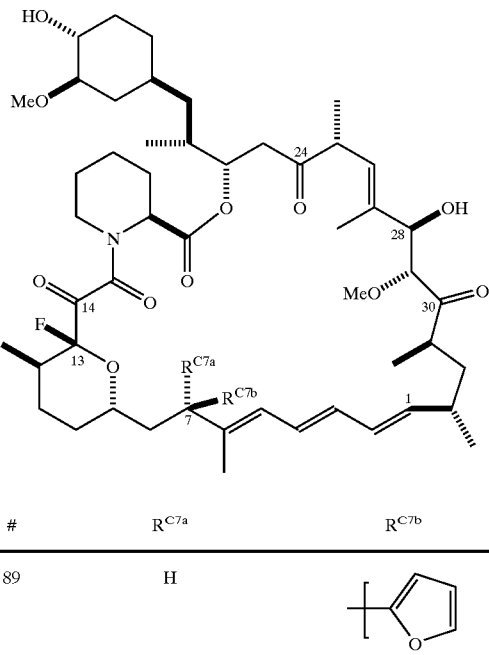

| # | $R^{C7a}$ | $R^{C7b}$ |
|---|---|---|
| 89 | H | 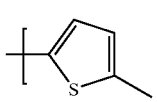 |
| 90 | (thiophene-methyl) | H |
| 91 | H | (methylthiophene) |
| 92 | (ethylthiophene) | H |

| # | R^C7a | R^C7b |
|---|---|---|
| 93 | H | 5-ethylthiophen-2-yl |
| 94 | 5-tBu-thiophen-2-yl | H |
| 95 | H | 5-tBu-thiophen-2-yl |
| 96 | -o,p-(MeO)₂phenyl | H |
| 97 | H | -o,p-(MeO)₂phenyl |
| 98 | indol-3-yl | H |
| 99 | H | indol-3-yl |
| 100 | -o,p-diethoxyphenyl | H |
| 101 | 3-methylthiophen-2-yl | H |
| 102 | pyrrol-2-yl | H |
| 103 | -2,4,6-(MeO)₃phenyl | H |
| 104 | H | -2,4,6-(MeO)₃phenyl |
| 105 | —NH—(C=O)—OEt | H |
| 106 | H | —NH—(C=O)—OEt |

Example 6.2

Compounds 81, 82—($R^{C7}$=Et) are synthesized as described in Example 3.1, but substituting 13-F-rapamycin (79) for rapamycin.

Example 6.3

Compound 83—($R^{C7}$=iPr) is synthesized as described in Example 3.2, but substituting 13-F-rapamycin (79) for rapamycin.

Example 6.4

Compound 84—($R^{C7}$=benzyl) is synthesized as described in Example 3.3, but substituting 13-F-rapamycin (79) for rapamycin.

Example 6.5

Compounds 85, 86—($R^{C7}$=—NH—CO—OMe) are synthesized as described in Example 3.4, but substituting 13-F-rapamycin (79) for rapamycin.

Example 6.6

Compound 87—($R^{C7}$=—NH—SO2-Me) is synthesized as described in Example 3.5, but substituting 13-F-rapamycin (79) for rapamycin.

Example 6.7

Compounds 88 and 89—($R^{C7}$=furanyl) are synthesized as described in Example 3.6, but substituting 13-F-rapamycin (79) for rapamycin.

Example 6.8

Compounds 90, 91—($R^{C7}$=methylthiophene) are synthesized as described in Example 3.7, but substituting 13-F-rapamycin (79) for rapamycin.

Example 6.9

Compounds 92, 93—($R^{C7}$=ethylthiophene) are synthesized as described in Example 3.8, but substituting 13-F-rapamycin (79) for rapamycin.

Example 6.10

Compounds 68, 69—($R^{C7}$=tertbutyl thiophene) are synthesized as described in Example 3.9, but substituting 13-F-rapamycin (79) for rapamycin.

Example 6.11

Compounds 94, 95—($R^{C7}$=o,p-dimethoxyphenyl) are synthesized as described in Example 3.10, but substituting 13-F-rapamycin (79) for rapamycin.

Example 6.12

Compounds 96, 97—($R^{C7}$=indolyl) are synthesized as described in Example 3.11, but substituting 13-F-rapamycin (79) for rapamycin.

Example 6.13

Compound 98—($R^{C7}$=o,p-diethoxyphenyl) is synthesized as described in Example 3.12, but substituting 13-F-rapamycin (79) for rapamycin.

Example 6.14

Compound 99—($R^{C7}$=methylthiophene) is synthesized as described in Example 3.13, but substituting 13-F-rapamycin (79) for rapamycin.

Example 6.15

Compound 100—($R^{C7}$=N-methylpyrrole) is synthesized as described in Example 3.14, but substituting 13-F-rapamycin (79) for rapamycin.

Example 6.20

Preparation of 28-F-rapamycin (107)

To a solution of rapamycin (71 mg, 0.078 mmol) in methylene chloride (1 mL) at −78° C. was added DAST (21 mL, 0.156 mmol) and reaction was allowed to stir for 2 h before MeOH was added to quench the reaction. The reaction mixture was taken to room temperature and stirred for 30 min. It was poured onto a biphasic solution of saturated aqueous NaHCO3 (20 mL) and EtOAc (30 mL). The organic layer was washed with additional solution of saturated aqueous NaHCO3 (2×20 mL) followed by a saturated aqueous solution of NaCl (2×10 mL) then dried over Na2SO4, filtered, evaporated. The resulting material was flash chromatographed on a silica gel (hexane:EtOAc, 1:1 to 1:2). MS, Fluorine NMR indicated C28 fluorinated rapamycin. Stereoisomers can be separated by reverse phase chromatography (C18 column, MeOH:H2O, 80:20), and may be used in place of rapamycin for the synthesis of various F-28 rapalogs.

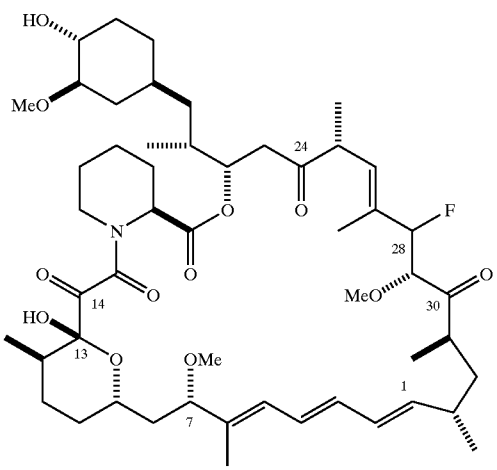

107

7. Assay of Human T-Cell Proliferation: a Mitogenesis Assay for Human Immunosuppressive Activity Primary human peripheral blood mononuclear cells are isolated from healthy donors using the Ficoll-Hypaque centrifugation procedure as recommended by the manufacturers (Pharmacis), washed in RPM1 complete medium and counted using Trypan blue. Aliquots (120 ul) of medium containing 1.2×105 cells are dispensed to the wells of a 96-well tissue culture plate that contain 120 ul of medium containing serial dilutions of rapamycin or rapalog in medium (<0.5% ethanol final concentration). The plate is incubated at 37° C. for one hour. Meanwhile, a second 96-well plate previously coated with an anti-human CD3 antibody is washed with medium, and 200 ul volumes of the preincubated cells transferred to the coated plate. Incubation is continued for 72 hours at 37° C., and then 20 ul of 50 uCi/ml of 3H-thymidine is added to each well. After overnight (12–16 hour) incubation, cells are harvested using an automated multiple cell harvester, and cell-associated radioactivity counted using a Beckman liquid scintillation counter. Results are expressed as the mean values derived from quadruplicate measurements. IC50 for proliferation inhibition is determined by the concentration of compound that leads to 50% reduction in specific cellular incorporation of 3H-thymidine, where 100% corresponds to the incorporation in the absence of compound.

Example 8

AF/IS Values for Representative Rapalogs

Three rapalogs of Formula II in which $R^{C7a}$ or $R^{C7b}$ is a substituted aryl or heteroaryl moiety were compared with rapamycin with respect to immunosuppressive activity as determined using a human peripheral lymphocyte proliferation assay and antifungal activity against clinical isolates of *Candida albicans, Cryptococcus neoformans* and *Aspergillus fumigatus* in a broth macrodilution assay as described previously. AF/IS values were calculated from the data obtained in one series of experiments and are tabulated below.

| Cmpd: | Rapamycin | A | B | C |
|---|---|---|---|---|
| R[C7a] | —OMe | -o,p-dimethoxy-phenyl | (thiophene-methyl group) | —H |
| R[C7b] | —H | —H | —H | (thiophene-ethyl group) |
| IS | 1 | <10[−3] | <10[−3] | <10[−3] |
| AF  I | 1 | <.5 | — | — |
| II | 1 | ≧1 | ≧2 | ≧2 |
| III | 1 | <0.5 | ≧0.2 | ≧1 |
| AF/IS  I | 1 | >1,000 | — | — |
| II | 1 | >1,000 | >1,000 | >1000 |
| III | 1 | >1,000 | >1,000 | >1000 |

I = *C. albicans*
II = *Cryptococcus neoformans*
III = *Asp fumigatus*

Example 9

Cloning an FRB Domain Homolog from *Cryptococcus neoformans*

Degenerate PCR primers were designed to amplify a region of FRAP encompassing the FRB domain by aligning known FRAP/RAFT/RAPT/TOR protein and nucleotide sequences and identifying short conserved regions. Sequences used included human, mouse, rat, *S. cerevisiae* and *C. albicans*. Primers 174 (annealing to regions encoding WYKAWHNW) and 176 (annealing to regions encoding DLELAVPGT) are shown below:

```
174     5'-TGGTAYAARGCNTGGCAYAAYTGGGC 176     5'-GTNCCNGGNACNGCYAAYTCYAARTC
``` where Y = C or T,
R = A or G,
and N = A, C, G or T.

These primers were used to amplify a portion of the FRAP homolog from a *C. neoformans* lambda cDNA library (strain B3501, Stratagene library #937052). A 'touchdown' PCR procedure using Taq polymerase (Boehringer Mannheim) was employed, with buffer conditions as recommended by the enzyme manufacturers and with a 'hot start'. The cycling regime was 5 minutes at 94° C., during which the enzyme was added; then 29 cycles of [94° C. 40 seconds, 60° C. 40 seconds, 72° C. 90 seconds] with the 60° C. anneal temperature lowered by 0.3° C. each cycle; then two cycles of [94° C. 40 seconds; then 50° C. 40 seconds]; and then 72° C. for ten minutes. A single product of the expected size (approximately 1074 bp) was obtained and cloned into the vector pCRII (In Vitrogen) using the TA cloning kit (Invitrogen). Four clones were sequenced by dideoxy sequencing and were found to be identical except for a single change at one position in one clone (TTT->CTT, encoding Phe->Leu), which may reflect a genuine polymorphism or a PCR error.

The nucleotide sequence and predicted protein sequence of the *C. neoformans* FRAP homolog is shown below. The position of the sequence variation noted above is underlined.

```
1/1                             31/11
acc cat aaa atg cga gag cac tct ccc aag atc gtt gac cag gcc gag ctt gtc agt act
 T   H   K   M   R   E   H   S   P   K   I   V   D   Q   A   E   L   V   S   T 61/21                           91/31
gag ctc atc cga gcg gct atc tta tgg cat gag atg tgg tat gat ggt ttg gaa gaa gcg
 E   L   I   R   A   A   I   L   W   H   E   M   W   Y   D   G   L   E   E   A 121/41                          151/51
tca aag cac tac ttt ggt gac cat gat atc cct ggc atg ctg gga gtt ctt gaa cct ttg
 S   K   H   Y   F   G   D   H   D   I   P   G   M   L   G   V   L   E   P   L 181/61                          211/71
cat gag att gtc gaa aac gga ccc caa acc ttg cgt gag acg tcc ttt att caa tcg ttc
 H   E   I   V   E   N   G   P   Q   T   L   R   E   T   S   F   I   Q   S   F 241/81                          271/91
ggg cat gat ttg cgt atc gcc cga gag cat ctc aag cgt tac cgt ata act cag gat ggg
 G   H   D   L   R   I   A   R   E   H   L   K   R   Y   R   I   T   Q   D   G 301/101                         331/111
acc gaa att caa caa gca tgg gat gtc tac tac tcc gtc ttc cag cgt ctc ggc aaa cag
 T   E   I   Q   Q   A   W   D   V   Y   Y   S   V   F   Q   R   L   G   K   Q
```

```
361/121                             391/131
ctc aag ctc ctg aac gtc att gag ctg caa tat gtc tcg ccc aag ttg atg gcc gtt cga
 L   K   L   L   N   V   I   E   L   Q   Y   V   S   P   K   L   M   A   V   R
```

What is claimed is:

1. A compound of the formula:

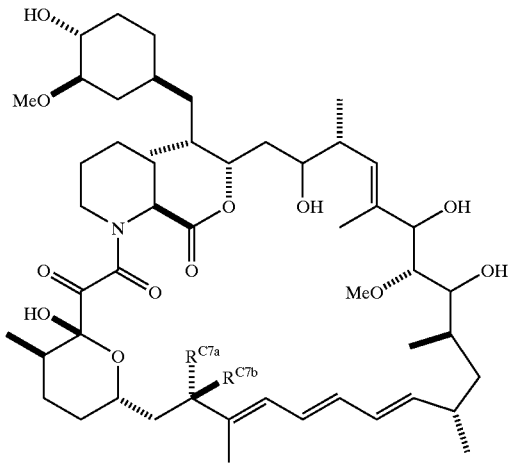

wherein one of $R^{C7a}$ and $R^{C7b}$ is H and the other is —H, halo, —OR$^1$, —SR$^1$, —OC(O)R$^1$, —OC(O)NHR$^1$, —NHR$^1$, —NHR$^1$R$^2$, —NHC(O)R$^1$, —NHSO$_2$R$^1$ or —R$^2$, where each occurrence of R$^1$ is H or an aliphatic, heteroaliphatic, aryl, or heteroaryl moiety, and each R$^2$ is an aliphatic, heteroaliphatic, aryl, heteroaryl or alkylaryl moiety;

where each ring substituent is present in either stereochemical orientation unless otherwise indicated;

or a pharmaceutically acceptable derivative thereof.

2. The compound of claim 1 in which one of $R^{C7a}$ and $R^{C7b}$ is H and the other is selected from substituted or unsubstituted alkenyl, aryl, heteroaryl or —Z-aliphatic, —Z-aryl, —Z-heteroaryl or —Z-acyl, where Z and Z' are independently O, S or NH; and acyl comprises —CHO, —C(=O)-aliphatic, —C(=O)-heteroaliphatic, —C(=O)-aryl, or —C(=O)-heteroaryl, —C(=O)—Z'-aliphatic, —C(=O)—Z'-aryl, or —C(=O)—Z'-heteroaryl.

3. The compound of claim 1 in which at least one of $R^{C7a}$ and $R^{C7b}$ is a moiety other than —OMe.

4. A compound of the formula:

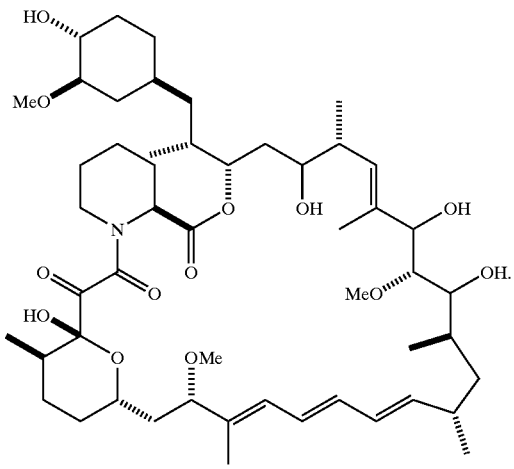

5. A derivative of the compound of claim 1 in which one or more of the hydroxyl groups are alkylated or replaced by an acyl, ester, carbamate, carbonate or urea moiety.

6. A derivative of the compound of claim 2 in which one or more of the hydroxyl groups are alkylated or replaced by an acyl, ester, carbamate, carbonate or urea moiety.

7. A derivative of the compound of claim 3 in which one or more of the hydroxyl groups are alkylated or replaced by an acyl, ester, carbamate, carbonate or urea moiety.

8. A derivative of the compound of claim 4 in which one or more of the hydroxyl groups are alkylated or replaced by an acyl, ester, carbamate, carbonate or urea moiety.

9. A composition comprising one or more compounds of any of claims 1–8 together with a pharmaceutically acceptable carrier or diluent and one or more optional pharmaceutically acceptable excipients.

* * * * *